US012239635B2

(12) United States Patent
Kim et al.

(10) Patent No.: US 12,239,635 B2
(45) Date of Patent: Mar. 4, 2025

(54) TREATMENT OF COGNITIVE DISORDERS USING NITAZOXANIDE (NTZ), NITAZOXANIDE (NTZ) ANALOGS, AND METABOLITES THEREOF

(71) Applicant: The Trustees of Columbia University in the City of New York, New York, NY (US)

(72) Inventors: Tae-Wan Kim, East Brunswick, NJ (US); Gina Finan, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 848 days.

(21) Appl. No.: 17/119,354

(22) Filed: Dec. 11, 2020

(65) Prior Publication Data

US 2021/0137896 A1 May 13, 2021

Related U.S. Application Data

(63) Continuation of application No. PCT/US2019/036753, filed on Jun. 12, 2019.

(60) Provisional application No. 62/685,113, filed on Jun. 14, 2018.

(51) Int. Cl.
*A61K 31/426* (2006.01)
*A61K 9/00* (2006.01)
*A61P 25/28* (2006.01)

(52) U.S. Cl.
CPC .......... *A61K 31/426* (2013.01); *A61K 9/0053* (2013.01); *A61P 25/28* (2018.01)

(58) Field of Classification Search
CPC ...... A61K 31/426; A61K 9/0053; A61P 25/28
USPC ........................................................ 514/365
See application file for complete search history.

(56) References Cited

U.S. PATENT DOCUMENTS

| | | | |
|---|---|---|---|
| 3,950,351 | A | 4/1976 | Rossignol et al. |
| 4,315,018 | A | 2/1982 | Rossignol |
| 5,387,598 | A | 2/1995 | Rossignol |
| 6,117,894 | A | 9/2000 | Rossignol |
| 8,124,632 | B2 | 2/2012 | Rossignol et al. |
| 8,524,278 | B2 | 9/2013 | Rossignol et al. |
| 2009/0036467 | A1 | 2/2009 | Rossignol et al. |
| 2011/0030137 | A1 | 2/2011 | McKenzie |
| 2013/0184353 | A1 | 7/2013 | Dickey et al. |
| 2014/0065215 | A1 | 3/2014 | Rossignol et al. |

FOREIGN PATENT DOCUMENTS

| | | |
|---|---|---|
| CN | 107375280 | 11/2017 |
| EP | 1555018 | 7/2005 |
| WO | 1996/019220 | 12/1995 |
| WO | 1998/050035 | 5/1998 |
| WO | 00/26202 | 5/2000 |
| WO | 2005/026137 | 3/2005 |
| WO | 2006/042195 | 10/2005 |
| WO | 2018/133884 | 11/2008 |
| WO | 2009/140621 | 11/2009 |
| WO | 2010/093854 | 8/2010 |
| WO | 2011/123916 | 4/2011 |
| WO | 2013/110975 | 1/2012 |
| WO | 2012/061190 | 5/2012 |
| WO | 2018/173069 | 9/2018 |
| WO | 2018/215795 | 11/2018 |
| WO | 2019/097050 | 5/2019 |

OTHER PUBLICATIONS

English translation of CN 107375280 A (Year: 2017).*
Advanced Drug Formulation Design to Optimize Therapeutic Outcomes, edited by Robert O. Williams, David R. Taft, and Jason T. McConville, including Table 2, p. 312.
Alamed, Jennifer, et al. "Two-day radial-arm water maze learning and memory task; robust resolution of amyloid-related memory deficits in transgenic mice." Nature protocols 1.4 (2006): 1671.
Amireddy, Niharika, et al. "The unintended mitochondrial uncoupling effects of the FDA-approved anti-helminth drug nitazoxanide mitigates experimental parkinsonism in mice." Journal of Biological Chemistry 292.38 (2017): 15731-15743.
Andrade Nunes, Marielza, Tania Araujo Viel, and Hudson Sousa Buck. "Microdose lithium treatment stabilized cognitive impairment in patients with Alzheimer's disease." Current Alzheimer Research 10.1 (2013): 104-107.
Ballatore, Carlo, Virginia M-Y. Lee, and John Q. Trojanowski. "Tau-mediated neurodegeneration in Alzheimer's disease and related disorders." Nature reviews neuroscience 8.9 (2007): 663-672.
Broekhuysen, J., et al. "Nitazoxanide: pharmacokinetics and metabolism in man." International journal of clinical pharmacology and therapeutics 38.8 (2000): 387-394.
Brunden, Kurt R., John Q. Trojanowski, and Virginia M-Y. Lee. "Advances in tau-focused drug discovery for Alzheimer's disease and related tauopathies." Nature reviews Drug discovery 8.10 (2009): 783-793.
Cordell, Cyndy B., et al. "Alzheimer's Association recommendations for operationalizing the detection of cognitive impairment during the Medicare Annual Wellness Visit in a primary care setting." Alzheimer's & Dementia 9.2 (2013): 141-150.
Égerházi, Anikó, et al. "Automated Neuropsychological Test Battery (CANTAB) in mild cognitive impairment and in Alzheimer's disease." Progress in Neuro-Psychopharmacology and Biological Psychiatry 31.3 (2007): 746-751.

(Continued)

*Primary Examiner* — Kristin A Vajda
(74) *Attorney, Agent, or Firm* — Baker Botts L.L.P

(57) ABSTRACT

Compounds and pharmaceutical compositions effective for treating cognitive disorders are described. The compounds and pharmaceutical compositions described include Nitazoxanide (NTZ), Nitazoxanide (NTZ) analogs, Nitazoxanide (NTZ) metabolites, or Nitazoxanide (NTZ) metabolite analogs. Methods of treating, ameliorating, and/or preventing cognitive disorders using the compounds and pharmaceutical compositions disclosed herein are also described.

18 Claims, 5 Drawing Sheets

(56) References Cited

OTHER PUBLICATIONS

Fan, Lei, et al. "Nitazoxanide, an anti-parasitic drug, efficiently ameliorates learning and memory impairments in AD model mice." Acta Pharmacologica Sinica 40.10 (2019): 1279-1291.

Farrer, Lindsay A., et al. "Assessment of genetic risk for Alzheimer's disease among first-degree relatives." Annals of Neurology: Official Journal of the American Neurological Association and the Child Neurology Society 25.5 (1989): 485-493.

Gilles, Herbert M., and Paul S. Hoffman. "Treatment of intestinal parasitic infections: a review of nitazoxanide." Trends in parasitology 18.3 (2002): 95-97.

Guidance for Industry: Estimating the Maximum Safe Starting Dose in Initial Clinical Trials for Therapeutics in Adult healthy Volunteers, Jul. 2005, U.S. Department of Health and Human Services Food and Drug Administration Center for Drug Evaluation and Research (CDER), 30 pages.

Hautala, Timo J., et al. "Nitazoxanide may modify the course of progressive multifocal leukoencephalopathy." Journal of clinical immunology 38.1 (2018): 4-6.

Haynes, Delia A., William Jones, and WD Samuel Motherwell. "Occurrence of pharmaceutically acceptable anions and cations in the Cambridge Structural Database." Journal of pharmaceutical sciences 94.10 (2005): 2111-2120.

Hsiao, Karen, et al. "Correlative memory deficits, Aβ elevation, and amyloid plaques in transgenic mice." Science 274.5284 (1996): 99-103.

Huttunen, Kristiina M., Hannu Raunio, and Jarkko Rautio. "Prodrugs—from serendipity to rational design." Pharmacological reviews 63.3 (2011): 750-771.

International Search Report and Written Opinion for PCT Patent Application No. PCT/US2019/036753, mailed Oct. 29, 2019; 19 pages.

Jack Jr, Clifford R., and David M. Holtzman. "Biomarker modeling of Alzheimer's disease." Neuron 80.6 (2013): 1347-1358.

Jack Jr, Clifford R., et al. "NIA-AA research framework: toward a biological definition of Alzheimer's disease." Alzheimer's & Dementia 14.4 (2018): 535-562.

Karch, Celeste M., Carlos Cruchaga, and Alison M. Goate. "Alzheimer's disease genetics: from the bench to the clinic." Neuron 83.1 (2014): 11-26.

Mandelkow, Eva-Maria, and Eckhard Mandelkow. "Biochemistry and cell biology of tau protein in neurofibrillary degeneration." Cold Spring Harbor perspectives in medicine 2.7 (2012): a006247.

Mann, David MA, and Margaret M. Esiri. "The pattern of acquisition of plaques and tangles in the brains of patients under 50 years of age with Down's syndrome." Journal of the neurological sciences 89.2-3 (1989): 169-179.

Marcelín-Jiménez, Gabriel, et al. "Development of a method by UPLC—MS/MS for the quantification of tizoxanide in human plasma and its pharmacokinetic application." Bioanalysis 4.8 (2012): 909-917.

Nair, Anroop B., and Shery Jacob. "A simple practice guide for dose conversion between animals and human." Journal of basic and clinical pharmacy 7.2 (2016): 27.

Newman, Mark F., et al. "Longitudinal assessment of neurocognitive function after coronary-artery bypass surgery." New England Journal of Medicine 344.6 (2001): 395-402.

Newman, Stanton, et al. "Postoperative cognitive dysfunction after noncardiac surgery: a systematic review." The Journal of the American Society of Anesthesiologists 106.3 (2007): 572-590.

Rasmussen, L. S., et al. "Does anaesthesia cause postoperative cognitive dysfunction? A randomised study of regional versus general anaesthesia in 438 elderly patients." Acta Anaesthesiologica Scandinavica 47.3 (2003): 260-266.

Roberson, Erik D., et al. "Reducing endogenous tau ameliorates amyloid β-induced deficits in an Alzheimer's disease mouse model." Science 316.5825 (2007): 750-754.

Rossignol, Jean François, et al. "Thiazolides, a new class of anti-influenza molecules targeting viral hemagglutinin at the post-translational level." Journal of Biological Chemistry 284.43 (2009): 29798-29808.

Rossignol, Jean-François. "Thiazolides: a new class of antiviral drugs." Expert opinion on drug metabolism & toxicology 5.6 (2009): 667-674.

Rossignol, J-F. "Nitazoxanide in the treatment of acquired immune deficiency syndrome-related cryptosporidiosis: results of the United States compassionate use program in 365 patients." Alimentary pharmacology & therapeutics 24.5 (2006): 887-894.

Ruiz-Olmedo, M. I., et al. "Sensitive high performance liquid chromatographic assay for nitazoxanide metabolite in plasma." Die Pharmazie—An International Journal of Pharmaceutical Sciences 64.7 (2009): 419-422.

Ruiz-Olmedo, María Isabel, et al. "Effect of nitazoxanide on albendazole pharmacokinetics in cerebrospinal fluid and plasma in rats." Saudi Pharmaceutical Journal 25.3 (2017): 413-418.

Sheehan, Bart. "Assessment scales in dementia." *Therapeutic advances in neurological disorders* 5.6 (2012): 349-358.

Stachulski, Andrew V., et al. "Second-generation nitazoxanide derivatives: thiazolides are effective inhibitors of the influenza A virus." Future medicinal chemistry 10.8 (2018): 851-862.

Stachulski, Andrew V., et al. "Thiazolides as novel antiviral agents. 1. Inhibition of hepatitis B virus replication." Journal of medicinal chemistry 54.12 (2011): 4119-4132.

Stockis, A., et al. "Nitazoxanide pharmacokinetics and tolerability in man during 7 days dosing with 0.5 g and 1 g bid." International journal of clinical pharmacology and therapeutics 40.5 (2002): 221-227.

Stockis, A., et al. "Pharmacokinetics of nitazoxanide after single oral dose administration in 6 healthy volunteers." International journal of clinical pharmacology and therapeutics 34.8 (1996): 349-351.

Stockis, Al, et al. "Nitazoxanide pharmacokinetics and tolerability in man using single ascending oral doses." International journal of clinical pharmacology and therapeutics 40.5 (2002): 213-220.

Strittmatter, Warren J., et al. "Apolipoprotein E: high-avidity binding to beta-amyloid and increased frequency of type 4 allele in late-onset familial Alzheimer disease." Proceedings of the National Academy of Sciences 90.5 (1993): 1977-1981.

Van Den Heuvel, Corinna, Emma Thornton, and Robert Vink. "Traumatic brain injury and Alzheimer's disease: a review." Progress in brain research 161 (2007): 303-316.

Van Duijn, C. M., and Theo Stijnen. "Risk factors for Alzheimer's disease: overview of the EURODEM collaborative re-analysis of case-control studies." International journal of epidemiology 20.Supplement_2 (1991): S4-S12.

Yankner, Bruce A. "Mechanisms of neuronal degeneration in Alzheimer's disease." Neuron 16.5 (1996): 921-932.

Zhao, Z., et al. "The pharmacokinetics of nitazoxanide active metabolite (tizoxanide) in goats and its protein binding ability in vitro." Journal of veterinary pharmacology and therapeutics 33.2 (2010): 147-153.

\* cited by examiner

Nitazoxanide $C_{12}H_{11}N_3O_5S$ MW = 307.28

Tizoxanide $C_{10}H_9N_3O_4S$ MW = 265.243

TREATMENT OF COGNITIVE DISORDERS USING NITAZOXANIDE (NTZ), NITAZOXANIDE (NTZ) ANALOGS, AND METABOLITES THEREOF

CROSS REFERENCE TO RELATED APPLICATIONS

This application is a continuation of International Application No. PCT/US2019/036753 filed Jun. 12, 2019, which claims the benefit of priority of U.S. Provisional Patent Application No. 62/685,113 filed Jun. 14, 2018, the contents of which are herein incorporated by reference in their entireties.

STATEMENT REGARDING FEDERALLY SPONSORED RESEARCH OR DEVELOPMENT

This invention was made with government support under NIH Grant Number NS074536 awarded by the National Institutes of Health. The government has certain rights in the invention.

FIELD OF THE INVENTION

The presently disclosed subject matter relates to compounds and pharmaceutical compositions useful for treating cognitive disorders such as Alzheimer's disease. The compounds and pharmaceutical compositions comprise Nitazoxanide (NTZ), Nitazoxanide (NTZ) analogs, and/or metabolites thereof. The present disclosure also relates to methods of treating, ameliorating, and/or preventing cognitive disorders such as Alzheimer's disease using the compounds and pharmaceutical compositions disclosed herein.

BACKGROUND

Cognitive disorders are characterized clinically by progressive loss of memory, cognition, reasoning, judgment and emotional stability that can gradually lead to profound mental deterioration including dementia and other neurodegenerative diseases.

Neurodegenerative diseases, also referred to as neurodegenerative disorders, are diseases that involve losses in the structure and/or function of neurons. Neurodegenerative diseases can be characterized by atypical protein assemblies in the brain and/or by neuron death. Neurodegenerative diseases can involve many different levels of neuronal activity, from molecular to systemic.

For example, Alzheimer's disease is a neurodegenerative disease that is the most common form of dementia. Alzheimer's disease is characterized by hallmark pathological lesions including amyloid plaques and neurofibrillary tangles consisting of aggregated amyloid-β peptide and tau, respectively. While neurodegeneration is a common feature for a number of neurodegenerative disorders, Alzheimer's disease is characterized by preferential glutamatergic neuronal loss in the brain regions that are involved with learning and memory including hippocampus and cortex. In contrast, for example, Parkinson's disease, a movement disorder, features the selective degeneration of dopaminergic neurons in the area of motor control such as mid-brain. Elevation and accumulation of amyloid-β in the brain are early and necessary steps in the pathogenesis of Alzheimer's disease, and precede all known clinical and pathological phenotypes of the disease, such as decline in memory and cognition, as well as tau pathology, by at least a decade. Amyloid-β is produced from the sequential proteolytic cleavage of β-amyloid precursor protein by a set of membrane-bound proteases termed β-secretase and γ-secretase.

Treatment of cognitive disorders, such as Alzheimer's disease, represents one of the biggest unmet needs in medicine today, due to rising life expectancy, a growing elderly population and no approved disease-modifying therapeutics. Drug development efforts for Alzheimer's disease have been characterized by largely unsuccessful clinical trials in the past decade. Accordingly, development of effective treatments for cognitive disorders such as Alzheimer's disease remains challenging.

SUMMARY

A method of treating a cognitive disorder in a subject in need thereof described herein includes administering to the subject an effective amount of a Nitazoxanide (NTZ) analog having Formula I:

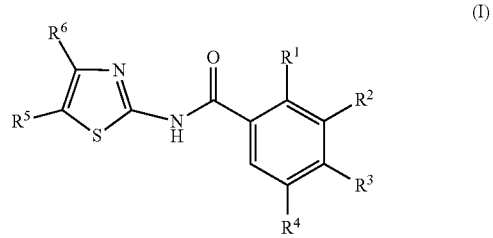

or a metabolite thereof, wherein $R^1$ can be selected from the group consisting of H, OH, OC(O)CH$_3$, and OC(O)CH$_2$CH$_3$; $R^2$, $R^3$, and $R^4$ can be independently selected from the group consisting of H, CH$_3$, OH, OCH$_3$, OC(O)CH$_3$, and halogen; $R^5$ can be selected from the group consisting of H, NO$_2$, halogen, optionally substituted alkyl, optionally substituted aryl, optionally substituted amido, optionally substituted sulfonyl, cyano, optionally substituted carboxy, and CF$_3$; and $R^6$ can be selected from the group consisting of H, Ph, and SO$_2$Me; or a salt, polymorph, solvate, hydrate, N-oxide, or co-crystal thereof.

A method of treating Alzheimer's disease in a subject in need thereof is also described, wherein the method includes administering to the subject an effective amount of a Nitazoxanide (NTZ) analog having Formula I, or a metabolite thereof, wherein $R^1$ can be selected from the group consisting of H, OH, OC(O)CH$_3$, and OC(O)CH$_2$CH$_3$; $R^2$, $R^3$, and $R^4$ can be independently selected from the group consisting of H, CH$_3$, OH, OCH$_3$, OC(O)CH$_3$, and halogen; $R^5$ can be selected from the group consisting of H, NO$_2$, halogen, optionally substituted alkyl, optionally substituted aryl, optionally substituted amido, optionally substituted sulfonyl, cyano, optionally substituted carboxy, and CF$_3$; and $R^6$ can be selected from the group consisting of H, Ph, and SO$_2$Me; or a salt, polymorph, solvate, hydrate, N-oxide, or co-crystal thereof.

The present disclosure also relates to a method of improving spatial working memory in a subject in need thereof. The method includes administering to the subject an effective amount of a Nitazoxanide (NTZ) analog having Formula I, wherein $R^1$ is selected from the group consisting of H, OH, OC(O)CH$_3$, and OC(O)CH$_2$CH$_3$; $R^2$, $R^3$, and $R^4$ are independently selected from the group consisting of H, CH$_3$, OH, OCH$_3$, OC(O)CH$_3$, and halogen; $R^5$ is selected from the group consisting of H, NO$_2$, halogen, optionally substituted alkyl, optionally substituted aryl, optionally substituted amido, optionally substituted sulfonyl, cyano, optionally substituted carboxy, and $CF_3$; and $R^6$ is selected from the group consisting of H, Ph, and $SO_2Me$; or a salt, polymorph, solvate, hydrate, N-oxide, or co-crystal thereof.

The present disclosure also relates to a method of performance in at least one cognitive test by a subject in need thereof. The method includes administering to the subject an effective amount of a Nitazoxanide (NTZ) analog having Formula I, wherein $R^1$ is selected from the group consisting of H, OH, $OC(O)CH_3$, and $OC(O)CH_2CH_3$; $R^2$, $R^3$, and $R^4$ are independently selected from the group consisting of H, $CH_3$, OH, $OCH_3$, $OC(O)CH_3$, and halogen; $R^5$ is selected from the group consisting of H, $NO_2$, halogen, optionally substituted alkyl, optionally substituted aryl, optionally substituted amido, optionally substituted sulfonyl, cyano, optionally substituted carboxy, and $CF_3$; and $R^6$ is selected from the group consisting of H, Ph, and $SO_2Me$; or a salt, polymorph, solvate, hydrate, N-oxide, or co-crystal thereof.

In any of the disclosed implementations, the method can further include the following details, which can be combined with either of the above methods and with one another in any combinations unless clearly mutually exclusive:
(i) $R^5$ of the Nitazoxanide (NTZ) analog can be selected from the group consisting of H, $NO_2$, iPr, $C_6H_4Cl$, NHAc, $SO_2CH_3$, CN, $CO_2CH_3$, $CF_3$, and Cl;
(ii) the Nitazoxanide (NTZ) analog can be Nitazoxanide (NTZ);
(iii) the effective amount of Nitazoxanide (NTZ) can be between 0.1 mg per day and 2000 mg per day;
(iv) the cognitive disorder can be Alzheimer's disease, prodromal Alzheimer's disease, dementia, degenerative disorders associated with learning, learning disabilities, memory or cognitive dysfunction, mild cognitive impairment, age-related cognitive decline, cerebral senility, vascular dementia, AIDS-associated dementia, memory impairment associated with depression or anxiety, Down's syndrome, stroke, traumatic brain injury, Huntington's disease, or attention deficit disorder, dementia lacking distinctive histology, progressive supranuclear palsy, corticobasal degeneration, argyrophilic grain disease, multiple system atrophy, amyotrophic lateral sclerosis, ataxia, familial British dementia, neurodegeneration with brain iron accumulation type 1, cerebral lipidoses, Tay-Sachs disease, Sandhoff disease, Gaucher disease, Niemann-Pick disease, Krabbe disease, neuronal ceroid lipofuscinoses, cerebrotendinous xanthomatosis, dementia in hepatic and renal failure, dementia due to chronic hypovitaminosis, metachromatic leukodystrophy, adrenoleukodystrophy, head trauma, Wernicke-Korsakoff syndrome, cerebral autosomal dominant arteriopathy with subcortical infarcts and leukoencephalopathy, Binswanger disease, cerebral amyloid angiopathy, cognitive dysfunction in multiple sclerosis, or normal pressure hydrocephalus;
(v) the Nitazoxanide (NTZ) analog having Formula I or a metabolite thereof can have negligible bioavailability in brain;
(vi) the Nitazoxanide (NTZ) analog having Formula I or a metabolite thereof can have a plasma concentration and a brain concentration, and the ratio between the plasma concentration and the brain concentration can be less than 0.02;
(vii) the Nitazoxanide (NTZ) analog having Formula I or a metabolite thereof can have a plasma concentration and a brain concentration, and the brain concentration is negligible when the plasma concentration is below about 300 ng/mL;
(viii) the administering to the subject an effective amount of the Nitazoxanide (NTZ) analog having Formula I or a metabolite thereof can ameliorate at least one cognitive deficit in the subject;
(ix) the cognitive deficit can be a spatial working memory deficit;
(x) the Nitazoxanide (NTZ) analog having Formula I or a metabolite thereof can be Tizoxanide (TIZ); and
(xi) the cognitive test can be a mini-mental state exam, a mini-cog test, a motor screening task, a paired associates learning test, a spatial working memory test, a reaction time test, a rapid visual information processing test, a delayed matching to sample test, a pattern recognition memory test, or an Automated Neuropsychological Test Battery (CANTAB).

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

Figure 1A:
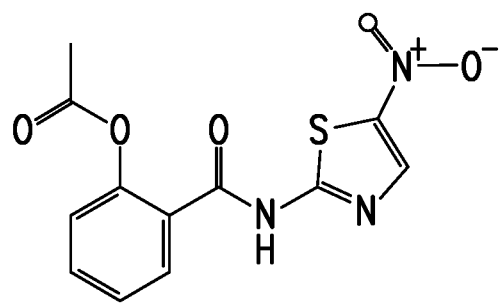
FIG. 1A is the chemical structure of Nitazoxanide (NTZ) and FIG. 1B is the chemical structure of its major metabolite Tizoxanide (TIZ)
Figure 1B:
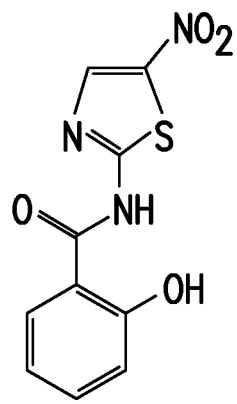

The presently disclosed subject matter relates to compounds and pharmaceutical compositions effective for treating cognitive disorders such as Alzheimer's disease. The compounds and pharmaceutical compositions described herein can include Nitazoxanide (NTZ), Nitazoxanide (NTZ) analogs, such as those having Formula I as disclosed herein, as well as metabolites thereof, such as the Tizoxanide (TIZ) and Tizoxanide glucuronide (TIZ-G) metabolites of Nitazoxanide (NTZ) and similar metabolites of Nitazoxanide (NTZ) analogs. The present disclosure also relates to methods of treating, ameliorating, and/or preventing Alzheimer's disease.

In particular, the present disclosure is directed to compositions and methods relating to the discovery that Nitazoxanide (NTZ), an FDA-approved compound previously used as an anti-protozoal agent, ameliorates cognitive impairment associated with Alzheimer's disease in a transgenic mouse model of Alzheimer's disease. In addition, the amelioration of cognitive impairment occurs despite negligible bioavailability of Nitazoxanide (NTZ) in brain.

A. Definitions

The terms "cognitive disorder", "cognitive impairment" and "cognitive deficits" indicate disruptions in performance including one or more of the following signs: (1) memory deficits (impaired ability to learn new information or recall previously learned information; (2) one (or more) of the following disturbances: a) aphasia (language disturbance); b) apraxia (impaired ability to carry out motor activities despite intact motor function); c) agnosia (failure to recognize or identify objects despite intact sensory function); d) disturbance in executive functioning (i.e. planning, organizing, sequencing, abstracting); (3) memory disturbances causing significant impairment in social or occupational functioning, and representing a significant decline from a previous level of functioning; and (4) impairment in cognitive functioning as evidenced by neuropsychological testing or quantified clinical assessment, accompanied by objective evidence of a systemic general medical condition or central nervous system dysfunction. The present disclosure relates to the use of Nitazoxanide (NTZ), Nitazoxanide (NTZ) analogs, and metabolites thereof for the treatment of impaired cognitive function in subjects or patients having a disorder including but not limited to Alzheimer's disease, learning disabilities caused by degenerative disorders, learning disabilities caused by non-degenerative disorders, memory or cognitive dysfunction such as mild cognitive impairment, age-related cognitive decline, cerebral senility, vascular dementia, AIDS-associated dementia, electric shock induced amnesia, memory impairment associated with depression or anxiety, Down's syndrome, stroke, traumatic brain injury, Huntington's disease, attention deficit disorder, dementia lacking distinctive histology, progressive supranuclear palsy, corticobasal degeneration, argyrophilic grain disease, multiple system atrophy, amyotrophic lateral sclerosis, ataxia, familial British dementia, thyroid disorders, neurodegeneration with brain iron accumulation type 1, cerebral lipidoses, Tay-Sachs disease, Sandhoff disease, Gaucher disease, Niemann-Pick disease, Krabbe disease, neuronal ceroid lipofuscinoses, cerebrotendinous xanthomatosis, dementia in hepatic and renal failure, dementia due to chronic hypovitaminosis, metachromatic leukodystrophy, adrenoleukodystrophy, head trauma, Wernicke-Korsakoff syndrome, cerebral autosomal dominant arteriopathy with subcortical infarcts and leukoencephalopathy, Binswanger disease, cerebral amyloid angiopathy, cognitive dysfunction in multiple sclerosis, and normal pressure hydrocephalus, among others identifiable by skilled persons.

According to the present disclosure, a "subject" or a "patient" is a human or non-human animal. Although the animal subject is preferably a human, the compounds and compositions of the invention have application in veterinary medicine as well, e.g., for the treatment of domesticated species such as canine, feline, murine, and various other pets; farm animal species such as bovine, equine, ovine, caprine, porcine, etc.; and wild animals, e.g., in the wild or in a zoological garden, such as non-human primates.

As used herein, the term "in need thereof" refers to the subject or patient who has been diagnosed with, identified with, or suspected of developing the disease, disorder, or condition referred to and requires or benefits from the treatment.

As used herein, the terms "treatment," "treating," and the like refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject or patient and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of a compound or composition that, when administered to a mammal or other subject for treating a disease, is sufficient to effect such treatment for the disease. The "therapeutically effective amount" can vary depending on compound or composition used, the disease and its severity, and the age, weight, etc., of the subject to be treated.

In particular, a therapeutically effective amount of the compounds and compositions described herein can be effective to improve one or more symptoms or signs of a cognitive disorder such as Alzheimer's disease in a subject such as a human patient. For example, a therapeutically effective amount can improve performance of a subject such as a human patient in one or more cognitive tests that can be administered to a subject such as an Alzheimer's disease patient. Examples of cognitive tests used for testing Alzheimer's disease patients include the mini-mental state exam, the mini-cog test, motor screening task, paired associates learning, spatial working memory, reaction time, rapid visual information processing, delayed matching to sample, and pattern recognition memory, among others identifiable by skilled persons. See, for example, Egerhazi, A., Berecz, R., Bartok, E., & Degrell, I. (2007). Automated Neuropsychological Test Battery (CANTAB) in mild cognitive impairment and in Alzheimer's disease. Progress in Neuro-Psychopharmacology and Biological Psychiatry, 31(3), 746-751, Sheehan, B, Assessment scales in dementia, Ther Adv Neurol Disord. 2012 November; 5(6): 349-358, and Cyndy B. Cordell, Soo Borson, Malaz Boustani, Joshua Chodosh, David Reuben, Joe Verghese, William Thies, Leslie B. Fried, Alzheimer's Association recommendations for operationalizing the detection of cognitive impairment during the Medicare Annual Wellness Visit in a primary care setting, Alzheimer's & Dementia 9 (2013) 141-150. For example, improvement in performance of one or more cognitive tests can be made in a cohort of subjects or patients treated with the compounds and compositions described herein in comparison to a cohort not treated with the compounds and compositions described herein. Improvement in performance of one or more of the cognitive tests can be made in a cohort of subjects or patients treated with the compounds and compositions described herein in comparison with performance of the same subjects or patients while not being treated with the compounds or compositions of the present disclosure (e.g. "on-drug" versus "off-drug"). Improvement in performance can be in comparison to predicted performance in absence of treatment, for example future performance based on presence of biomarkers, for example during prodromal Alzheimer's disease, early Alzheimer's disease or MCI. Improvement can be by a detectable statistically significant or non-statistically significant amount and can be, for example, about a 1%, 2%, 3%, 4% 5%, 6%, 7%, 8%, 9%, 10% or more improvement in performance. Improvement in performance can be measured over a period of about a week, a month, a year or several years, following initiation of treatment. Appropriate time frames for ascertaining treatment effects in a subject such as an Alzheimer's disease patient are identifiable by skilled persons upon reading of the present disclosure.

As would be understood by persons skilled in the art, deficiencies in cognitive performance in cognitive disorders such as Alzheimer's disease occurs over a continuum, however cognitive performance can be categorized into cognitive staging, such as cognitively unimpaired, MCI, mild dementia, moderate dementia, and severe dementia, for example as described in Jack et al., NIA-AA Research Framework: Toward a biological definition of Alzheimer's disease. Alzheimers Dement. 2018 April; 14(4): 535-562.

In particular, as a general guideline, the term "cognitively unimpaired" or "age-related cognitive decline" can refer to cognitive performance within an expected range for that individual based on all available information, including the age of the individual. This can be based on clinical judgment and/or on cognitive test performance (which may or may not be based on comparison to normative data, with or without adjustments for age, education, occupation, sex, etc.). Cognitive performance can be in the impaired/abnormal range based on population norms but performance is within the range expected for that individual.

As a general guideline, the terms "mild cognitive impairment" or "MCI" as used herein can refer to cognitive performance below an expected range for that individual based on all available information, including the age of the individual. This can be based on clinical judgment and/or on cognitive test performance (which may or may not be based on comparison to normative data with or without adjustments for age, education, occupation, sex, etc.). Cognitive performance is usually in the impaired/abnormal range based on population norms but this is not required as long as is performance is below the range expected for that individual. In addition to evidence of cognitive impairment, evidence of decline in cognitive performance from baseline is typically also present. This can be reported by the individual or by an observer (e.g. study partner) or observed by change on longitudinal cognitive testing/behavioral assessments or by a combination of these. MCI can be characterized by cognitive presentations that are not primarily amnestic. Although cognitive impairment is the core clinical criteria, neurobehavioral disturbance can be a prominent feature of the clinical presentation. Individuals with MCI can perform daily life activities independently but cognitive difficulty can result in detectable but mild functional impact on the more complex activities of daily life, either self-reported or corroborated by a study partner.

As a general guideline, the term "dementia" can refer to substantial progressive cognitive impairment that affects several domains and/or neurobehavioral symptoms. Dementia can be reported by the individual or by an observer (e.g. study partner) or observed by change on longitudinal cognitive testing. Dementia includes cognitive impairment and/or neurobehavioral symptoms resulting in clearly evident functional impact on daily life. Demented individuals are no longer fully independent and generally require assistance with daily life activities, which can be considered the primary feature differentiating dementia from MCI. Dementia can be subdivided into mild, moderate and severe. In general, individuals with "mild dementia" have substantial progressive cognitive impairment affecting several domains, and/or neurobehavioral disturbance. Mild dementia can be documented by the individual's report or by observer (e.g. study partner) report or by change on longitudinal cognitive testing. Mild dementia can be indicated by clearly evident functional impact on daily life, affecting mainly instrumental activities. Individuals with mild dementia may be no longer fully independent and may require occasional assistance with daily life activities. In general, individuals with "moderate dementia" have progressive cognitive impairment or neurobehavioral changes. Moderate dementia can be indicated by extensive functional impact on daily life with impairment in basic activities. Individuals with moderate dementia are generally no longer independent and require frequent assistance with daily life activities. In general, individuals with "severe dementia". have progressive cognitive impairment or neurobehavioral changes. Clinical interview of individuals with severe dementia may not be possible. Individuals with severe dementia in general have complete dependency due to severe functional impact on daily life with impairment in basic activities, including basic self-care.

The term "halogen" refers to fluorine, chlorine, bromine, and iodine.

The term "alkyl" refers to a straight or branched C1-C20, preferably C1-C5, hydrocarbon group consisting solely of carbon and hydrogen atoms, containing no unsaturation, and which is attached to the rest of the molecule by a single bond, e.g., methyl, ethyl, n-propyl, 1-methylethyl (isopropyl, also denoted as i-propyl or iPr), n-butyl, n-pentyl, and 1,1-dimethylethyl (t-butyl).

The term "aryl" refers to aromatic radicals having in the range of about 6 to about 14 carbon atoms such as phenyl, naphthyl, tetrahydronapthyl, indanyl, and biphenyl.

The term "alkenyl" refers to a $C_2$-$C_{20}$, preferably $C_1$-$C_5$, aliphatic hydrocarbon group containing at least one carbon-carbon double bond and which can be a straight or branched chain, e.g., ethenyl, 1-propenyl, 2-propenyl (allyl), isopropenyl, 2-methyl-1-propenyl, 1-butenyl, and 2-butenyl.

The term "cycloalkyl" refers to an unsaturated, non-aromatic mono- or multicyclic hydrocarbon ring system such as cyclopropyl, cyclobutyl, cyclopentyl, cyclohexyl. Examples of multicyclic cycloalkyl groups include perhydronaphthyl, adamantyl and norbornyl groups bridged cyclic group or sprirobicyclic groups, e.g., spiro (4,4) non-2-yl.

The term "amido" refers to a moiety that can be represented by the formula $-NR^7C(O)R^8$ or $-C(O)NR^9R^{10}$, wherein $R^7$, $R^8$, $R^9$, and $R^{10}$ can independently be H, alkyl, aryl, alkenyl, or cycloalkyl, as defined above.

The term "sulfonyl" refers to a moiety that can be represented by the formula $-SO_2R^{11}$, wherein $R^{11}$ can be H, alkyl, aryl, alkenyl, or cycloalkyl, as defined above.

The term "carboxy" refers to a moiety that can be represented by the formula $-CO_2R^{12}$, wherein $R^{12}$ can be H, alkyl, aryl, alkenyl, or cycloalkyl, as defined above.

The term "Ac" refers to an acetyl group ($-C(O)CH_3$). The term "Me" refers to a methyl group ($CH_3$). The term "Et" refers to an ethyl group ($CH_2CH_3$).

The term "optionally substituted" indicates that a moiety can be substituted with zero, one, or more than one substituents. The substituents in the "substituted alkyl," "substituted alkenyl," "substituted cycloalkyl," "substituted aryl," "substituted amido," "substituted sulfonyl," and "substituted carboxy" groups can be the same or different, with one or more selected from the groups hydrogen, halogen, acetyl (Ac), nitro ($NO_2$), oxo ($=O$), $CF_3$, $NH_2$, $OCH_3$, or optionally substituted groups selected from alkyl, alkoxy and aryl.

The terms "pharmaceutical composition" and "pharmaceutical formulation," as used herein, refer to a composition which is in such form as to permit the biological activity of an active ingredient contained therein to be effective, and which contains no additional components which are unacceptably toxic to a subject or a patient to which the formulation would be administered.

The term "pharmaceutically acceptable," as used herein, e.g., with respect to a "pharmaceutically acceptable carrier," refers to the property of being nontoxic to a subject or a patient. A pharmaceutically acceptable ingredient in a pharmaceutical formulation can be an ingredient other than an active ingredient which is nontoxic. A pharmaceutically acceptable carrier can include a buffer, excipient, stabilizer, and/or preservative.

B. Nitazoxanide (NTZ), Nitazoxanide (NTZ) Analogs and Nitazoxanide (NTZ) Metabolites Nitazoxanide (NTZ) is a compound that belongs to the thiazolide class of compounds and can more specifically be characterized as a nitrothiazolyl-salicylamide drug compound. Nitazoxanide (NTZ) is also known by the trade names ALINIA® (Romark Laboratories, L.C. Corporation, Florida, US) and by the chemical name [2-[(5-nitro-1,3-thiazol-2-yl)carbamoyl]phenyl]ethanoate. Nitazoxanide (NTZ) has the structure:

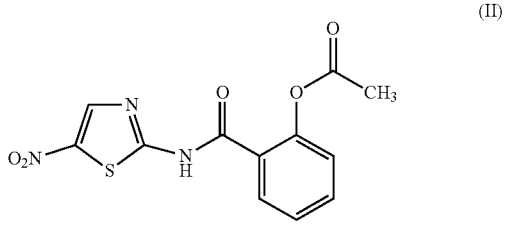 [SMILES: CC(=O)Oc1ccccc1C(=O)Nc1ncc([N+](=O)[O-])s1]

(II)

Nitazoxanide (NTZ) is an anti-protozoal agent. See Gilles H M, Hoffman P S. Treatment of intestinal parasitic infections: a review of Nitazoxanide (NTZ). Trends Parasitol. 2002 March; 18(3):95-7. PMID: 11854075 and Rossignol J F. Nitazoxanide (NTZ) in the treatment of acquired immune deficiency syndrome-related cryptosporidiosis: results of the United States compassionate use program in 365 patients. Aliment Pharmacol Ther. 2006 Sep. 1; 24(5):887-94. PMID: 16918894. Nitazoxanide (NTZ) is approved for treatment of infectious diarrhea caused by *Cryptosporidium parvum* and *Giardia lamblia* in patients 1 year of age and older.

Following oral administration Nitazoxanide (NTZ) is rapidly hydrolyzed to its active metabolite, Tizoxanide (TIZ), which is 99% protein bound. Tizoxanide (TIZ) can be further metabolized to its glucuronide (Tizoxanide glucuronide, also known as TIZ-G). Tizoxanide (TIZ) has the structure:

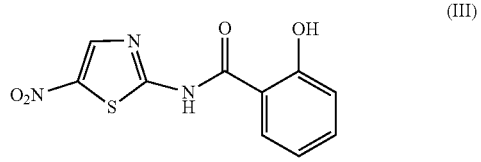 [SMILES: O=C(Nc1ncc([N+](=O)[O-])s1)c1ccccc1O]

(III)

Tizoxanide (TIZ) is an active compound and can itself be administered to a subject or a patient as an active pharmaceutical ingredient.

Nitazoxanide (NTZ) and Nitazoxanide (NTZ) analogs are also being developed as anti-viral agents. See Rossignol J F. Thiazolides: a new class of antiviral drugs. Expert Opin Drug Metab Toxicol. 2009 June; 5(6):667-74. doi: 10.1517/17425250902988487. Review. PMID: 19442032 and Stachulski A V, Pidathala C, Row E C, Sharma R, Berry N G, Iqbal M, Bentley J, Allman S A, Edwards G, Helm A, Hellier J, Korba B E, Semple J E, Rossignol J F. Thiazolides as novel antiviral agents. 1. Inhibition of hepatitis B virus replication. J Med Chem. 2011 Jun. 23; 54(12):4119-32. doi: 10.1021/jm200153p. Epub 2011 May 23. PMID: 21553812. Nitazoxanide (NTZ) is metabolized into Tizoxanide (TIZ) and its glucuronide (TIZ-G). They are well-tolerated and have excellent pharmacokinetic profiles in humans. See Stockis A, De Bruyn S, Gengler C, Rosillon D. Nitazoxanide pharmacokinetics and tolerability in man during 7 days dosing with 0.5 g and 1 g b.i.d. Int J Clin Pharmacol Ther. 2002a May; 40(5):221-7. PMID: 12051574; Stockis A, Allemon A M, De Bruyn S, Gengler C. Nitazoxanide pharmacokinetics and tolerability in man using single ascending oral doses. Int J Clin Pharmacol Ther. 2002a May; 40(5): 213-20. PMID: 12051573; Broekhuysen J, Stockis A, Lins R L, De Graeve J, Rossignol J F. Nitazoxanide: pharmacokinetics and metabolism in man. Int J Clin Pharmacol Ther. 2000 August; 38(8):387-94. PMID: 10984012; Stockis A, Deroubaix X, Lins R, Jeanbaptiste B, Calderon P, Rossignol J F. Pharmacokinetics of Nitazoxanide (NTZ) after single oral dose administration in 6 healthy volunteers. Int J Clin Pharmacol Ther. 1996 August; 34(8):349-51. PMID: 8864798; Zhao Z, Xue F, Zhang L, Zhang K, Fei C, Zheng W, Wang X, Wang M, Zhao Z, Meng X. The pharmacokinetics of Nitazoxanide (NTZ) active metabolite (tizoxanide) in goats and its protein binding ability in vitro. J Vet Pharmacol Ther. 2010 April; 33(2):147-53. doi: 10.1111/j.1365-2885.2009.01119.x. PMID: 20444039; Ruiz-Olmedo M I, Gallegos-Perez J L, Calderon-Gonzalez K G, Franco-Perez J, Jung-Cook H. Sensitive high performance liquid chromatographic assay for Nitazoxanide (NTZ) metabolite in plasma. Pharmazie. 2009 July; 64(7):419-22. PMID: 19694176; and Marcelin-Jimenez G, Contreras-Zavala L, Maggi-Castellanos M, Angeles-Moreno A P, Garcia-Gonzalez A. Development of a method by UPLC-MS/MS for the quantification of tizoxanide in human plasma and its pharmacokinetic application. Bioanalysis. 2012 May; 4(8):909-17. doi: 10.4155/bio.12.41. PMID: 22533565.

Nitazoxanide (NTZ) analogs having the general structural formula of Formula I:

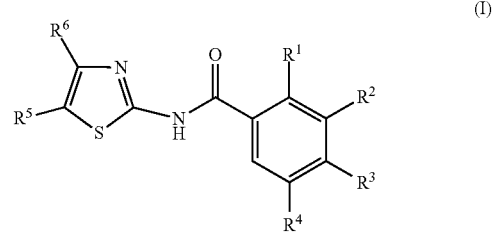

(I)

have been described in the art.

U.S. Pat. No. 3,950,351 describes Nitazoxanide (NTZ) and Nitazoxanide (NTZ) analogs. U.S. Pat. No. 3,950,351 also describes the synthesis of said compounds. The Nitazoxanide (NTZ) analogs disclosed in U.S. Pat. No. 3,950,351 are suitable for use in the methods and compositions of the present disclosure. The Nitazoxanide (NTZ) analogs disclosed in U.S. Pat. No. 3,950,351 are of the general structural formula of Formula I and are presented in Table 1.

TABLE 1

Nitazoxanide (NTZ) and Nitazoxanide (NTZ) analogs described in U.S. Pat. No. 3,950,351.

| Compound Code Number (U.S. Pat. No. 3,950,351) | $R^1$ (Formula I) | $R^2$ (Formula I) | $R^3$ (Formula I) | $R^4$ (Formula I) | $R^5$ (Formula I) | $R^6$ (Formula I) |
|---|---|---|---|---|---|---|
| PH 5776 (Nitazoxanide, NTZ) | $OC(O)CH_3$ | H | H | H | $NO_2$ | H |
| PH 6049 | $OC(O)CH_2CH_3$ | H | H | H | $NO_2$ | H |
| PH 6045 | H | $OC(O)CH_3$ | H | H | $NO_2$ | H |
| PH 6046 | H | H | $OC(O)CH_3$ | H | $NO_2$ | H |
| PH 6056 | $OC(O)CH_3$ | H | H | $OC(O)CH_3$ | $NO_2$ | H |
| PH 6058 | $OC(O)CH_3$ | H | $OC(O)CH_3$ | H | $NO_2$ | H |
| PH 6059 | H | $OCH_3$ | H | $OCH_3$ | $NO_2$ | H |
| PH 6057 | $OC(O)CH_3$ | H | H | Cl | $NO_2$ | H |
| PH 6103 | $OC(O)CH_3$ | H | H | Br | $NO_2$ | H |
| PH 6161 | H | $OC(O)CH_3$ | H | $OC(O)CH_3$ | $NO_2$ | H |
| PH 6162 | H | $OC(O)CH_3$ | $OC(O)CH_3$ | H | $NO_2$ | H |
| PH 6177 | H | $OC(O)CH_3$ | $OC(O)CH_3$ | $OC(O)CH_3$ | $NO_2$ | H |
| PH 6196 | H | $OCH_3$ | $OC(O)CH_3$ | H | $NO_2$ | H |
| PH 6239 | $OC(O)CH_3$ | $OC(O)CH_3$ | H | H | $NO_2$ | H |

Rossignol J F, La Frazia S, Chiappa L, Ciucci A, Gabriella Santoro M, Thiazolides, a New Class of Anti-influenza Molecules Targeting Viral Hemagglutinin at the Post-translational Level, J. Biol. Chem. (2009) 284:29798-29808 ("Rossignol et al., J. Biol. Chem 2009") describes Nitazoxanide (NTZ) and Nitazoxanide (NTZ) analogs. The Nitazoxanide (NTZ) analogs described therein are suitable for use in the methods and compositions of the present disclosure. The Nitazoxanide (NTZ) analogs disclosed in Rossignol et al., J. Biol. Chem 2009 are of the general formula of Formula I and are presented in Table 2.

TABLE 2

Nitazoxanide (NTZ) and Nitazoxanide (NTZ) analogs described in Rossignol et al., J. Biol. Chem 2009.

| Compound Code Number Rossignol et al., J. Biol. Chem 2009 | $R^1$ (Formula I) | $R^2$ (Formula I) | $R^3$ (Formula I) | $R^4$ (Formula I) | $R^5$ (Formula I) | $R^6$ (Formula I) |
|---|---|---|---|---|---|---|
| Nitazoxanide (NTZ) | $OC(O)CH_3$ | H | H | H | $NO_2$ | H |
| Tizoxanide (TIZ) | OH | H | H | H | $NO_2$ | H |
| RM4803 | $OC(O)CH_3$ | $CH_3$ | H | H | Br | H |
| RM4832 | OH | H | H | H | Br | H |
| RM4850 | OH | H | H | $CH_3$ | Cl | H |
| RM4865 | $OC(O)CH_3$ | H | H | $CH_3$ | Cl | H |
| RM5014 | $OC(O)CH_3$ | H | H | H | H | $SO_2CH_3$ |

Stachulski et al., Thiazolides as Novel Antiviral Agents: I. Inhibition of Hepatitis B Virus Replication, J. Med. Chem. (2011) 54: 4119-4132 ("Stachulski et al., J. Med. Chem. 2011") describes Nitazoxanide (NTZ) and Nitazoxanide (NTZ) analogs. The Nitazoxanide (NTZ) analogs described therein are suitable for use in the methods and compositions of the present disclosure. The Nitazoxanide (NTZ) analogs disclosed in Stachulski et al., J. Med. Chem. 2011 are of the general formula of Formula I and are presented in Table 3.

TABLE 3

Nitazoxanide (NTZ) and Nitazoxanide (NTZ) analogs described in Stachulski et al., J. Med. Chem. 2011.

| Compound Code Number Stachulski et al., J. Med. Chem. 2011 | $R^1$ (Formula I) | $R^2$ (Formula I) | $R^3$ (Formula I) | $R^4$ (Formula I) | $R^5$ (Formula I) | $R^6$ (Formula I) |
|---|---|---|---|---|---|---|
| 1 (Nitazoxanide, NTZ) | $OC(O)CH_3$ | H | H | H | $NO_2$ | H |
| 2 (Tizoxanide, TIZ) | OH | H | H | H | $NO_2$ | H |
| 3 | OH | H | H | H | Cl | H |
| 4 | OH | $CH_3$ | H | H | $NO_2$ | H |
| 5 | OH | H | $CH_3$ | H | $NO_2$ | H |
| 6 | OH | H | H | H | Br | H |
| 7 | OH | $CH_3$ | H | H | Br | H |
| 8 | OH | Cl | H | H | Br | H |
| 9 | OH | H | F | H | Br | H |
| 10 | OH | H | H | Cl | Br | H |
| 11 | OH | $CH_3$ | H | H | Cl | H |
| 12 | OH | H | H | $CH_3$ | Cl | H |
| 13 | OH | H | $CH_3$ | H | Cl | H |
| 14 | OH | H | H | H | F | H |
| 16 | OH | H | H | H | H | H |
| 17 | OH | H | H | H | iPr | H |
| 18 | OH | H | H | H | $C_4H_6Cl$ | H |
| 19 | OH | H | H | H | H | Ph |
| 20 | OH | $CH_3$ | H | H | H | Ph |
| 21 | OH | Cl | H | H | H | Ph |
| 22 | H | H | OH | H | $NO_2$ | H |
| 23 | OH | H | H | H | NHAc | H |
| 24 | OH | H | H | H | H | $SO_2CH_3$ |
| 25 | OH | H | H | H | $SO_2CH_3$ | H |
| 26 | OH | H | H | H | CN | H |
| 27 | OH | H | H | H | $CO_2Me$ | H |
| 28 | OH | H | H | H | $CF_3$ | H |
| 29 | $OCO_2Et$ | H | H | H | $NO_2$ | H |

The Nitazoxanide (NTZ) analog can be compound number 24 of Stachulski et al., J. Med. Chem. 2011, wherein $R^1$ is OH, $R^2$ is H, $R^3$ is H, $R^4$ is H, $R^5$ is H, and $R^6$ is $SO_2CH_3$. This compound is also known as RM5015. The Nitazoxanide (NTZ) analog can be compound number 25 of Stachulski et al., J. Med. Chem. 2011, wherein $R^1$ is OH, $R^2$ is H, $R^3$ is H, $R^4$ is H, $R^5$ is $SO_2CH_3$, and $R^6$ is H. This compound is also known as RM4863. Preparation of these compounds (RM5015 and RM4863) is also described in U.S. Patent Application Publication No. US 2009/0036467 A1 and in International (PCT) Publication No. WO 2012/061190 A1.

$R^5$ of the Nitazoxanide (NTZ) analog can be selected from the group consisting of H, $NO_2$, iPr, $C_6H_4Cl$, NHAc, $SO_2CH_3$, CN, $CO_2CH_3$, $CF_3$, and Cl.

Stachulski A V, Santoro M G, Piacentini S, Belardo G, Frazia S, Pidathala C, Row E C, Berry N G, Iqbal M, Allman S A, Semple J E, Eklov B M, O'Neill P M, Rossignol J F. Second-generation Nitazoxanide (NTZ) derivatives: thiazolides are effective inhibitors of the influenza A virus. Future Med Chem. 2018 Apr. 9 ("Stachulski et al., Future Med Chem. 2018") describes Nitazoxanide (NTZ) derivatives. The Nitazoxanide (NTZ) analogs described therein are suitable for use in the methods and compositions of the present disclosure. The Nitazoxanide (NTZ) analogs disclosed in Stachulski et al., Future Med Chem. 2018 are of the general formula of Formula I and are presented in Table 4.

TABLE 4

Nitazoxanide (NTZ) and Nitazoxanide (NTZ) analogs described in Stachulski et al., Future Med Chem. 2018.

| Compound Code Number (Stachulski et al., Future Med Chem. 2018) | $R^1$ (Formula I) | $R^2$ (Formula I) | $R^3$ (Formula I) | $R^4$ (Formula I) | $R^5$ (Formula I) | $R^6$ (Formula I) |
|---|---|---|---|---|---|---|
| 1 | OAc | H | H | H | $NO_2$ | H |
| 2 | OH | H | H | H | $NO_2$ | H |
| 8 | H | H | OH | H | $NO_2$ | H |
| 9 | OH | Me | H | H | $NO_2$ | H |
| 3 | OAc | H | H | H | Cl | H |
| 4 | OAc | H | H | H | Br | H |
| 10 | OAc | Me | H | H | Cl | H |
| 11 | OAc | H | H | H | H | SMe |
| (±)12 | OAc | H | H | H | H | SOMe |
| 5 | OAc | H | H | H | H | $SO_2Me$ |
| 13 | OAc | H | H | H | H | $SO_2Et$ |
| 14 | OH | H | H | H | $SO_2Me$ | H |
| 15 | OH | H | H | H | CN | H |
| 16 | OH | H | H | H | $CO_2Me$ | H |
| 17 | OAc | H | H | H | $CF_3$ | H |
| 18 | OAc | H | H | H | H | $CF_3$ |
| 19 | OH | H | H | H | H | H |

The compounds of the present disclosure can include structural variations of the compounds to provide for pro-drug forms. For example, but not by way of limitation, such pro-drug forms can provide for improved oral delivery. The design of such pro-drugs is outlined in Huttunen et al., "Prodrugs—from Serendipity to Rational Design", Pharmacological Reviews September vol. 63 no. 3 750-771 (2011), which is herein incorporated by reference in its entirety.

Salts of the Nitazoxanide (NTZ) analogs can include pharmaceutically acceptable salts. By way of non-limiting example, salts of the Nitazoxanide (NTZ) analogs can include salts described in Haynes, D. A., Jones, W. and Motherwell, W. D. S. (2005), Occurrence of pharmaceutically acceptable anions and cations in the Cambridge Structural Database. J. Pharm. Sci., 94: 2111-2120.

It was previously suggested that Nitazoxanide (NTZ) is a highly bioavailable drug when administered orally, and can reach the central nervous system. See, for example, Amireddy N, Puttapaka S N, Vinnakota R L, Ravuri H G, Thonda S, Kalivendi S V. J Biol Chem. 2017 Sep. 22; 292(38):15731-15743.

In order to experimentally assess levels of Nitazoxanide (NTZ) in brain of treated animals, pharmacokinetic experiments were performed following oral dosing of rats and mice with Nitazoxanide (NTZ) (see Example 3 and Example 4). In contrast to expectations based on the literature, it was found that brain-to-plasma ratio (B/P) ratio values are 0.015 in mouse and 0.008 in rat, indicating that Nitazoxanide (NTZ) does not penetrate into the brain to exert direct pharmacological effects in the CNS (see FIGS. 4-5 and Tables 5-6). In addition, computation of the log BB value, an index of blood-brain-barrier (BBB) permeability, of Nitazoxanide (NTZ), Tizoxanide (TIZ) and Tizoxanide glucuronide (TIZ-G), revealed no or low permeation based on the Pipeline Pilot Chemistry ADMET Collection from Biovia (http://accelrys.com/products/collaborative-science/databases/bioactivity-databases/) and Computational Chemical Genomics Screening Center (CCGS) (http://www.cbligand.org/BBB/predictor.php). These data suggest that Nitazoxanide (NTZ) can exert therapeutic efficacy by ameliorating memory impairments in a mouse model of Alzheimer's disease (see Examples 1 and 2) by functioning at the level of the peripheral system without entering the brain.

As would be understood by skilled persons, the results described herein indicating negligible bioavailability of the compounds in brains of mice and rats are expected to correlate with negligible bioavailability of the same compounds in human brain following similar administration, e.g. orally, in a subject such as a human patient.

Accordingly, in a subject such as a human patient, administration of the compounds and compositions described herein are expected to improve cognitive performance in a cognitive disorder such as Alzheimer's disease while having negligible bioavailability in brain. The term "negligible" as used herein can indicate absence of a pharmaceutically effective amount in brain. For example, the term negligible as used herein in regard to the amount of drug present in brain can indicate a measurable concentration of 0 or not significantly different from 0. For example, as described in Examples 3 and 4, a negligible amount can be about 0-20 ng/mL, for example as measured by HPLC/MS/MS analysis. Negligible bioavailability in brain can be indicated by a low brain/plasma ratio, such as a brain/plasma ratio less than 0.1, less than 0.05, or less than 0.02.

Methods of detecting the compounds described herein in brain and plasma include those described in Examples 3 and 4, such as by HPLC/MS/MS analysis, among other techniques identifiable by skilled persons.

For example, as shown in Examples 3 and 4, a negligible amount of the compound in brains of rats and mice can be indicated wherein a plasma concentration is approximately 200-300 ng/mL in rats and mice. Equivalent values in human patients are identifiable by persons of ordinary skill in the art, for example using methods of extrapolating from animal values to human values, as described herein. For example, concentration of the Nitazoxanide (NTZ) analogs and metabolites thereof described herein in brain of a human patient is expected to be negligible following administration of a pharmaceutically effective dose of the Nitazoxanide (NTZ) analogs and metabolites thereof (e.g., between 0.1 mg and 2000 mg).

C. Methods of Use

Types of Alzheimer's disease that can be treated, ameliorated, and/or prevented according to the methods of the present disclosure include late onset, early onset, sporadic, and/or familial Alzheimer's disease. Types of Alzheimer's disease that can be treated, ameliorated, and/or prevented according to the methods of the present disclosure include mild, moderate and severe Alzheimer's disease, prodromal Alzheimer's disease, mild cognitive impairment (MCI), pre-symptomatic Alzheimer's disease harboring disease-causing mutations, and/or conditions related to Alzheimer's disease-associated risk alleles. Pre-symptomatic Alzheimer's disease can be identified by detection of biomarkers correlated with Alzheimer's disease, which can include amyloid-β42 in cerebrospinal fluid (CSF), increased levels of CSF total (t-tau) and phosphorylated (p-tau) tau, imaging of amyloid by positron emission tomography (PET), imaging of hypometabolism by fludeoxyglucose PET, and imaging of atrophy by structural MRI. See Jack C R Jr, Holtzman D M. Neuron. 2013 Dec. 18; 80(6):1347-58. doi: 10.1016/j.neuron.2013.12.003. Review. PMID: 24360540 As would be understood by skilled persons, the term "amyloid-β42" as used herein indicates a 42 amino acid fragment that is a major component of amyloid plaques, and accumulates in neurons of Alzheimer's disease brains.

The present disclosure provides for methods of treating a subject or a patient at elevated risk of developing Alzheimer's disease. Individuals at elevated risk of amyloid-β accumulation can be subjects or patients at elevated risk of developing Alzheimer's disease. Such individuals can include those who carry a copy of the apolipoprotein E4 gene (see Strittmatter et al., (1993) Proc. Natl. Acad. Sci. U.S.A. 90, 1977-1981), those with trisomy 21 (Down's syndrome) (see Mann and Esiri, (1989) J. Neurol. Sci. 89, 169-179)), and those who carry a mutation in one of the genes that encode the amyloid precursor protein, presenilin-1 or presenilin-2 (see Yankner, B. A. (1996) Neuron 16, 921-932). In addition, individuals with a family history of Alzheimer's can be at increased risk of Alzheimer's disease (see Farrer et al., (1989) Ann. Neurol. 25, 485-492 and van Duijn et al., (1991) Int. J. Epidemiol. 20 (suppl 2), S13-S20), and can therefore benefit from treatment according to the present invention. For a summary of genetic risks associated with Alzheimer's disease, see also Karch C M, Cruchaga C, Goate A M. Alzheimer's Disease Genetics: From the Bench to the Clinic. Neuron. 2014 Jul. 2; 83(1):11-26.PMID: 24991952. Subjects or patients with high levels apoE4 and high cholesterol, defined as a blood cholesterol level of greater than 200 mg/dl, can also be at elevated risk of developing Alzheimer's disease and can also benefit from treatment according to the present invention. Other conditions can also elevate risk of Alzheimer's disease. Subjects or patients who have had strokes can be at elevated risk for Alzheimer's disease and related disorders. Subjects or patients who have been exposed to anesthesia can be at elevated risk of Alzheimer's disease and related disorders. See Newman, M. F., Kirchner, J. L., Phillips-Bute, B. et al. Longitudinal assessment of neurocognitive function after coronary-artery bypass surgery. N Engl J Med. 2001; 344: 395-402; Newman, S., Stygall, J., Hirani, S., Shaefi, S., and Maze, M. Postoperative cognitive dysfunction after noncardiac surgery: a systematic review. Anesthesiology. 2007; 106: 572-590; and Rasmussen, L. S., Johnson, T., Kuipers, H. M. et al. Does anaesthesia cause postoperative cognitive dysfunction? a randomised study of regional versus general anaesthesia in 438 elderly patients. Acta Anaesthesiol Scand. 2003; 47: 260-266. Subjects or patients who have suffered head injury can be at elevated risk of Alzheimer's disease and related disorders. See, for example, Van Den Heuvel, C, Thornton, E, Vink, R, Progress in Brain Research Volume 161, 2007, Pages 303-316. Subjects or patients with prodromal Alzheimer's disease or mild cognitive impairment (MCI) can be at elevated risk of developing more severe Alzheimer's disease and/or related disorders.

Methods of treating a subject or a patient with a cognitive disorder such as Alzheimer's disease can include diagnosing a subject or a patient with a cognitive disorder such as Alzheimer's disease and administering to the subject or a patient an effective amount of a Nitazoxanide (NTZ) analog. The methods described herein can include diagnosing a subject or a patient with Alzheimer's disease. Methods of diagnosing a subject or a patient with Alzheimer's disease are known in the art and can include measurement of elevated levels in cerebrospinal fluid and/or measurement of mutations in the genes for two of the proteins that make up the cytochrome oxidase complex in mitochondria of subjects or patients with Alzheimer's disease. Additional methods of diagnosing a subject or a patient with Alzheimer's disease are known and can include diagnosing a subject or a patient with dementia, measuring a subject's or a patient's progressive physical and mental deterioration, and/or excluding other possible causes of the foregoing conditions. Diagnosing a subject or a patient with Alzheimer's disease and/or elevated risk of Alzheimer's disease can include identifying certain biomarkers correlated with Alzheimer's disease and/or elevated risk of Alzheimer's disease. Biomarkers correlated with Alzheimer's disease and/or elevated risk of Alzheimer's disease can include cerebrospinal fluid (CSF) biochemical markers (e.g. Abeta and tau), amyloid imaging by positron emission tomography (PET), brain atrophy measured by structural MRI, hypometabolism of the brain measured by FDG PET measuring, and cognitive impairments measured by neurological testing. For general description of Biomarker Modeling of Alzheimer's Disease, see Jack et al. 2013 Neuron 80(6):1347-58. PMID: 24360540.

In general, Alzheimer's disease can also be defined by various biomarker and cognitive diagnostic criteria as described in Jack et al., NIA-AA Research Framework: Toward a biological definition of Alzheimer's disease. Alzheimers Dement. 2018 April; 14(4):535-562. doi: 10.1016/j.jalz.2018.02.018, the contents of which is herein incorporated by reference in its entirety.

Methods of treating a subject or a patient with Alzheimer's disease can include administering to the subject or the patient a therapeutically effective amount of a Nitazoxanide (NTZ) analog, wherein the compound is administered in a suitable dosage and in the form of a pharmaceutical composition, as noted below. The Nitazoxanide (NTZ) analog can be administered systemically (e.g., by intravenous injection, oral administration, inhalation, etc.), intraventricularly, intrathecally, transdermally, intradermally, intranasally, or by any other means known in the art.

The method of treating a subject or a patient with Alzheimer's disease can include administering to the subject or the patient a therapeutically effective amount of at least one additional therapeutic agent in addition to a Nitazoxanide (NTZ) analog. Non-limiting examples of additional therapeutic agents can include a compound for the treatment of Alzheimer's disease, such as an acetylcholinesterase inhibitor or an NMDA glutamate receptor antagonist (e.g., memantine). When Nitazoxanide (NTZ) analogs are administered in combination with one or more additional therapeutic agents, the compounds can be administered in either order or simultaneously. A Nitazoxanide (NTZ) analog can be combined with tau immunotherapy reagents (e.g., antibody therapies) and/or Amyloid beta immunotherapy reagents (e.g., antibody therapies).

The Nitazoxanide (NTZ) analog can be administered to the subject or the patient one time or over a series of treatments. For example, but not by way of limitation, the Nitazoxanide (NTZ) analog and/or pharmaceutical formulation thereof, as disclosed herein, can be administered to a subject three times every day, twice every day, once every day, once every two days, once every three days, once every four days, once every five days, once every six days, once a week, once every two weeks, once every three weeks, once every month, once every two months, once every three months, once every six months, or once every year.

Pharmaceutically acceptable dosages of Nitazoxanide (NTZ) and other Nitazoxanide (NTZ) analogs are described. See, for example and not by way of limitation, U.S. Pat. Nos. 3,950,351; 4,315,018; 5,387,598; Stachulski et al., J. Med.

Chem. 2011; and Rossignol et al., J. Biol. Chem 2009. Pharmaceutically acceptable dosages for a subject or a human patient can be in a range or about in a range from 0.1 mg per day to 2000 mg per day. The dosage can be in a range or about in a range from 0.1 mg per day to 5 mg per day, e.g., from 0.1 mg per day to 0.5 mg per day, or 0.5 mg per day to 1 mg per day, or 1 mg per day to 2 mg per day, or 2 mg per day to 3 mg per day, or 3 mg per day to 4 mg per day, or 4 mg per day to 5 mg per day. The dosage can be in a range or about in a range from 5 mg per day to 100 mg per day, e.g., from 5 mg per day to 10 mg per day, or 10 mg per day to 20 mg per day, or 20 mg per day to 30 mg per day, or 30 mg per day to 40 mg per day, or 40 mg per day to 50 mg per day, or 50 mg per day to 75 mg per day, or 75 mg per day to 100 mg per day. The dosage can be in a range or about in a range from 100 mg per day to 500 mg per day, e.g., from 100 mg per day to 125 mg per day, or 125 mg per day to 150 mg per day, or 150 mg per day to 175 m per day g, or 175 mg per day to 200 mg per day, or 200 mg per day to 250 mg per day, or 250 mg per day to 300 mg per day, or 300 mg per day to 350 mg per day, or 350 mg per day to 400 mg per day, or 400 mg per day to 450 mg per day, or 450 mg per day to 500 mg per day. The dosage can be in a range or about in a range from 500 mg per day to 1000 mg per day, e.g., from 500 mg per day to 600 mg per day, or 600 mg per day to 700 mg per day, or 700 mg per day to 800 mg per day, or 800 mg per day to 900 mg per day, or 900 mg per day to 1000 mg per day. The dosage can be in a range or about in a range from 1000 mg per day to 1500 mg per day, e.g., from 1000 mg per day to 1100 mg per day, or 1100 mg per day to 1200 mg per day, or 1200 mg per day to 1300 mg per day, or 1300 mg per day to 1400 mg per day, or 1400 mg per day to 1500 mg per day. The dosage can be in a range or about in a range from 1500 mg per day to 2000 mg per day, e.g., from 1500 mg per day to 1600 mg per day, or 1600 mg per day to 1700 mg per day, or 1700 mg per day to 1800 mg per day, or 1800 mg per day to 1900 mg per day, or 1900 mg per day to 2000 mg per day. The dosage can be tailored to the body weight of a subject or a human patient. For example, the dosage can be in a range or about in a range from 0.5 mg/(kg*day) to 100 mg/(kg*day).

A therapeutically effective amount of Nitazoxanide (NTZ) for administration to a subject or a human patient can be identified by persons of ordinary skill in the art. In particular, a therapeutically effective amount for use in humans can be identified by extrapolation from a therapeutically effective amount in an animal. For example, see Nair, A B and Jacob S, A simple practice guide for dose conversion between animals and human, J Basic Clin Pharm. March 2016-May 2016; 7(2): 27-31 and Guidance for Industry: Estimating the Maximum Safe Starting Dose in Initial Clinical Trials for Therapeutics in Adult healthy Volunteers, July 2005, U.S. Department of Health and Human Services Food and Drug Administration Center for Drug Evaluation and Research (CDER).

As shown in Example 2, Nitazoxanide (NTZ) is effective to improve cognitive performance in a transgenic mouse model of Alzheimer's disease when administered at a dose of 40 mg/kg/day, but not when administered at 400 mg/kg/day. Accordingly, persons of ordinary skill in the art can determine an equivalent dose in a subject or a human patient that is effective to improve cognitive performance in a subject or a human patient upon reading the present disclosure.

D. Pharmaceutical Compositions

The Nitazoxanide (NTZ) analogs of the present disclosure can be formulated as pharmaceutical compositions or pharmaceutical formulations by admixture with a pharmaceutically acceptable carrier or excipient. The pharmaceutical formulations can include one or more Nitazoxanide (NTZ) analogs and a physiologically acceptable diluent or carrier. The pharmaceutical composition can further include a second drug, for example, but not by way of limitation, a compound for the treatment of Alzheimer's disease, such as an acetylcholinesterase inhibitor or an NMDA glutamate receptor antagonist (e.g., memantine).

For general guidance on formulation of central nervous system drugs and drug delivery, see Advanced Drug Formulation Design to Optimize Therapeutic Outcomes, edited by Robert O. Williams, David R. Taft, and Jason T. McConville, including Table 2, p. 312.

The pharmaceutical formulation can be a solid dosage form. The solid dosage form can be a tablet or capsule. The tablet can be an immediate release tablet. The tablet can be an extended or controlled release tablet. The solid dosage can include both an immediate release portion and an extended or controlled release portion. The solid dosage form can include one or more Nitazoxanide (NTZ) analogs in an immediate release portion and one or more Nitazoxanide (NTZ) analogsn an extended or controlled release portion; the compound(s) of the immediate release portion and the compound(s) of the extended or controlled release can be the same or different. See, for example, WO 2010093854 A1.

The pharmaceutical formulation can be a liquid formulation. The liquid formulation can be an oral solution or oral suspension.

The pharmaceutical formulation can be a transdermal drug delivery system, e.g., a patch, cream, gel, and/or microemulsion.

The pharmaceutical formulation can include liposomes, nanoparticles, and/or other carriers. The pharmaceutical formulation can include an adjuvant or enhancer, e.g., an enzyme inhibitor.

The pharmaceutical formulation can be a direct infusion. The pharmaceutical formulation can be an implantable device.

EXAMPLES

The following examples are put forth so as to provide those of ordinary skill in the art with a complete disclosure and description of how to make and use the presently disclosed subject matter and are not intended to limit the scope of what the inventors regard as their presently disclosed subject matter. It is understood that various other embodiments can be practiced, given the general description provided above.

Example 1. Nitazoxanide (NTZ) Restores Spatial Working Memory Deficits in a Tg2576 Mouse Model of Alzheimer's Disease when Administered Via Oral Gavage Nitazoxanide (NTZ) was shown to restore spatial working memory deficits in a Tg2576 mouse model of Alzheimer's disease. In order to test the preclinical efficacy of Nitazoxanide (NTZ) in Alzheimer's disease mouse models, Tg2576 mice were treated. Tg2576 mice are a mouse model of Alzheimer's disease. See Hsiao K, Chapman P, Nilsen S, Eckman C, Harigaya Y, Younkin S, Yang F, Cole G (1996) Correlative memory deficits, Abeta elevation, and amyloid plaques in transgenic mice. Science 274:99-102. Adult transgenic (Tg2576) and wild-type mice were used, aged 7-10 months (WT-Control, n=16; Tg-Control, n=18; Tg-N1, n=12). Mice were housed in an animal room maintained at 22±2° C., a relative humidity of 50±10%, and a 12-h light/dark automatic light cycle. All animals were allowed free access to food and water. Nitazoxanide (NTZ) (also referred to herein as N1) was suspended in 0.5% carboxymethylcellulose (CMC) and administered via oral gavage at 100 mg/kg/day for 14 days, and throughout testing. For spatial working memory testing, two-day radial arm water maze (RAWM) was performed as previously described. See Alamed J, Wilcock D M, Diamond D M, Gordon M N, Morgan D. Two-day radial-arm water maze learning and memory task; robust resolution of amyloid-related memory deficits in transgenic mice. Nat Protoc. 2006; 1(4):1671-9. The radial arm water maze consisted of a 1 m pool with six swim paths (arms) radiating out of an open central area, with a hidden escape platform located at the end of one of the arms. On each trial, the mouse was allowed to swim in the pool for up to 60 seconds to find the escape platform. Incorrect arm entries or failure to select an arm for 10 seconds were counted as errors. On day 1, mice were given 15 trials where each block consisted of three trials (five blocks in total) alternating between a visible platform (above the water) and a hidden platform (below the water). The following day, mice were given 15 additional trials (five blocks), all using a hidden platform. Swim speed was tested using a visible platform task in which mice were to locate a visible platform in an open pool. Three (3) trials were performed per session (3 sessions total). The task was recorded and scored using EthoVision XT 8.0 video tracking software (Noldus Information Technology). For statistical analysis of RAWM testing, one-way AVONA was used followed by Fisher's LSD post hoc test.

Figure 2B:
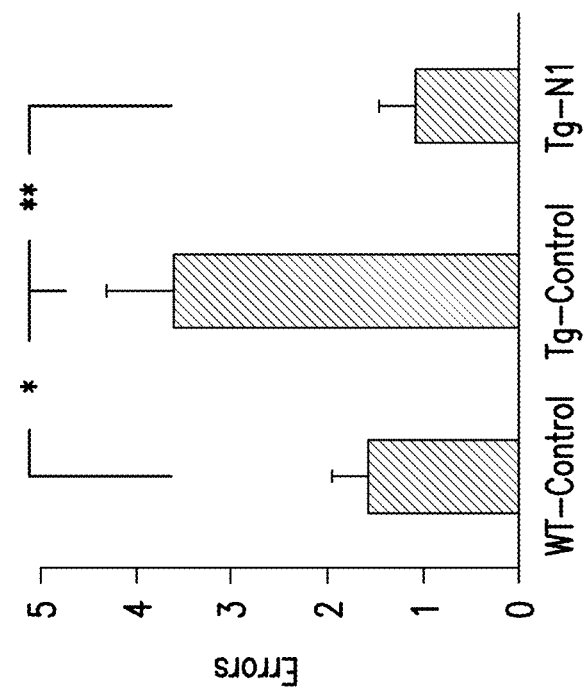
FIG. 2A, FIG. 2B and FIG. 2C are graphs reporting exemplary data of effects of Nitazoxanide (NTZ) administered via oral gavage on spatial working memory deficits in a Tg2576 mouse model of Alzheimer's disease.
Figure 2A:
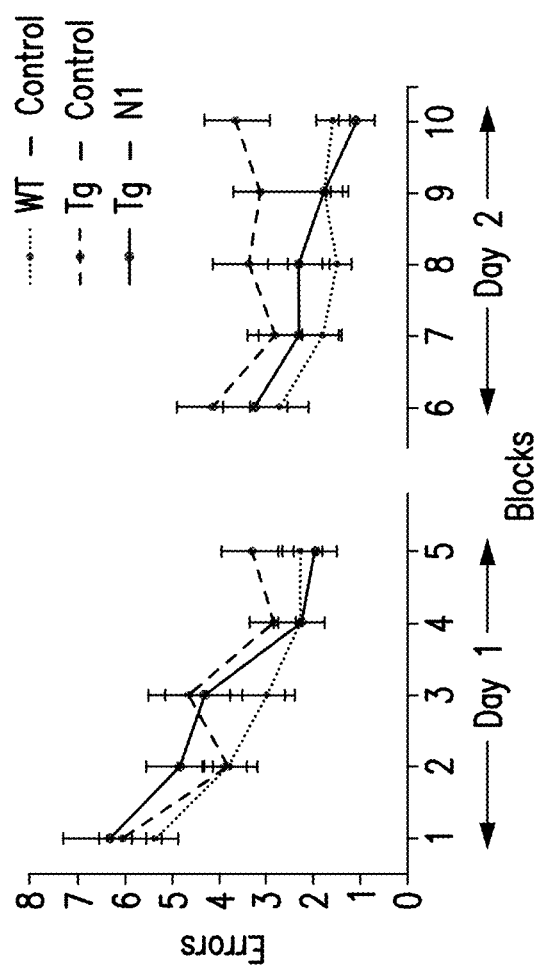
Figure 2C:
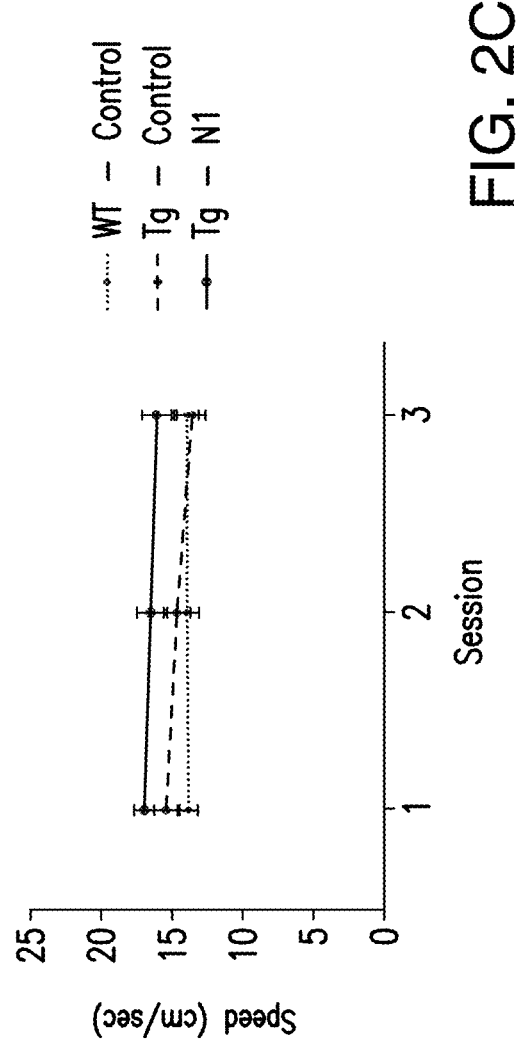

The results of the study are presented in FIG. 2A, FIG. 2B and FIG. 2C. The exemplary results reported in FIG. 2A and FIG. 2B show that control-treated transgenic mice were impaired in the radial arm maze, making significantly more errors than WT mice, and transgenic mice treated with Nitazoxanide (NTZ) performed similarly to WT mice, making significantly fewer errors than control-treated transgenic mice. The results reported in FIG. 2C show that swimming speed was similar in all three groups of mice. The results reported in FIG. 2A, FIG. 2B and FIG. 2C indicate that Nitazoxanide (NTZ) ameliorates spatial working memory deficits in this transgenic mouse model of Alzheimer's disease.

Example 2. Nitazoxanide (NTZ) Restores Spatial Working Memory Deficits in a T22576 Mouse Model of Alzheimer's Disease when Administered in Chow An additional cohort of Tg2576 and wild-type mice were tested in the RAWM, aged 7-10 months (WT-Control, n=8; Tg-Control, n=4; Tg-NTZ 40 mg/kg/d, n=6; Tg-NTZ 400 mg/kg/d, n=5). All animals were allowed free access to food and water. Nitazoxanide (NTZ) was administered via chow at 40 or 400 mg/kg/day for 3 months. For spatial working memory testing, two-day radial arm water maze (RAWM) was performed as previously described (47). Briefly, the radial arm water maze consists of a 1 m pool with six swim paths (arms) radiating out of an open central area, with a hidden escape platform located at the end of one of the arms. On each trial, the mouse was allowed to swim in the pool for up to 60 seconds to find the escape platform. Incorrect arm entries or failure to select an arm for 10 seconds were counted as errors. On day 1, mice were given 15 trials where each block consists of three trials (five blocks in total) alternating between a visible platform (above the water) and a hidden platform (below the water). The following day, mice were given 15 additional trials (five blocks), all using a hidden platform. (B) Quantification of trial #10 of the RAWM. (C) Swim speed was tested using a visible platform task in which mice were to locate a visible platform in an open pool. 3 trials were performed per session (3 sessions total). The task was recorded and scored using EthoVision XT 8.0 video tracking software (Noldus Information Technology). For statistical analysis of RAWM testing, one-way AVONA was used followed by Fisher's LSD post hoc test.

Figure 3B:
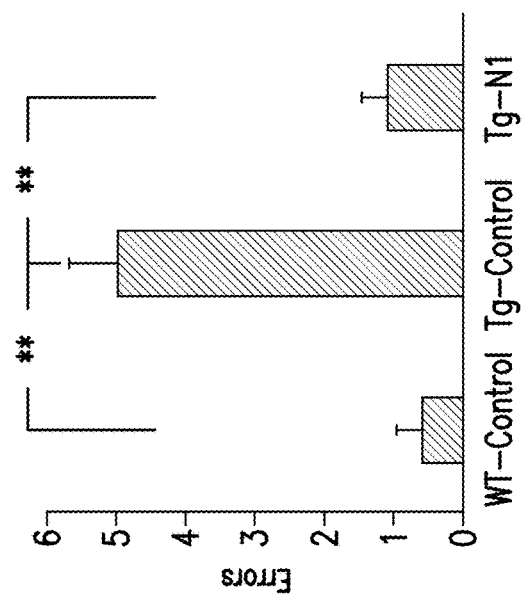
FIG. 3A, FIG. 3B and FIG. 3C are graphs reporting exemplary data of effects of Nitazoxanide (NTZ) administered in chow on spatial working memory deficits in a Tg2576 mouse model of Alzheimer's disease.
Figure 3A:
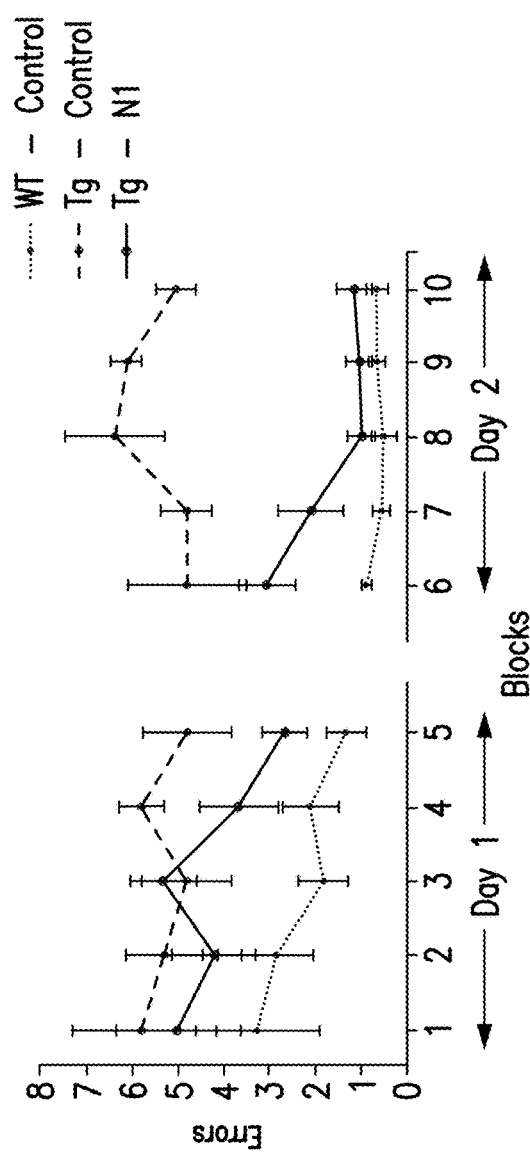
Figure 3C:
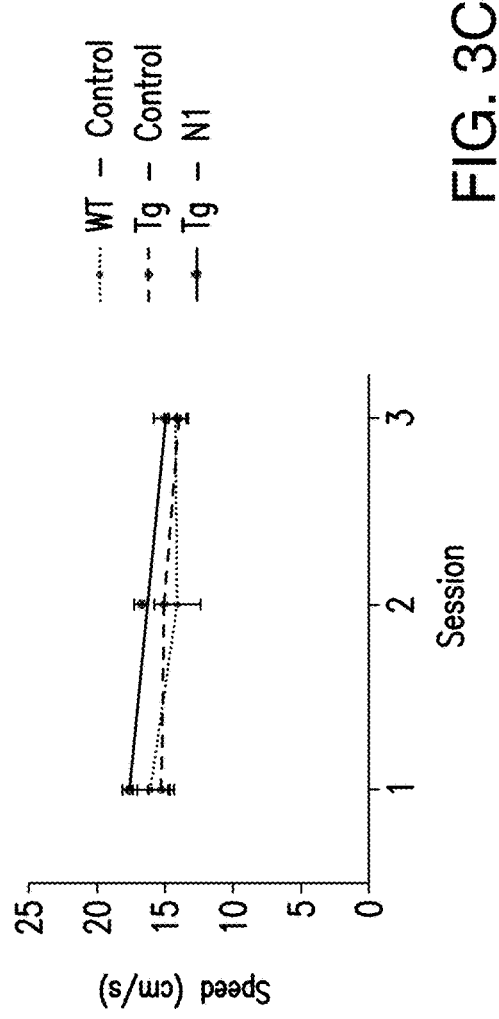

The results of the study are presented in FIG. 3A, FIG. 3B and FIG. 3C. The exemplary results reported in FIG. 3A and FIG. 3B show that control-treated transgenic mice were impaired in the radial arm maze, making significantly more errors than WT mice, and transgenic mice treated with Nitazoxanide (NTZ) at 40 mg/kg/day performed similarly to WT mice, making significantly fewer errors than control-treated transgenic mice. However, transgenic mice treated with Nitazoxanide (NTZ) at 400 mg/kg/day performed similarly to control-treated transgenic mice. The results reported in FIG. 3C show that swimming speed was similar in all three groups of mice. The results reported in FIG. 3A, FIG. 3B and FIG. 3C indicate that Nitazoxanide (NTZ) administered at 40 mg/kg/day ameliorates spatial working memory deficits in this transgenic mouse model of Alzheimer's disease, whereas Nitazoxanide (NTZ) administered at 400 mg/kg/day did not ameliorate spatial working memory deficits in this transgenic mouse model of Alzheimer's disease.

Example 3. Pharmacokinetics of Tizoxanide (TIZ) after Oral Administration of Nitazoxanide (NTZ) Pill (Alinia) in Rat A pharmacokinetic experiment was performed to determine Tizoxanide (TIZ, active metabolite of Nitazoxanide, NTZ) in rat brain and plasma following oral administration to Sprague Dawley (SD) rat.

Figure 4:
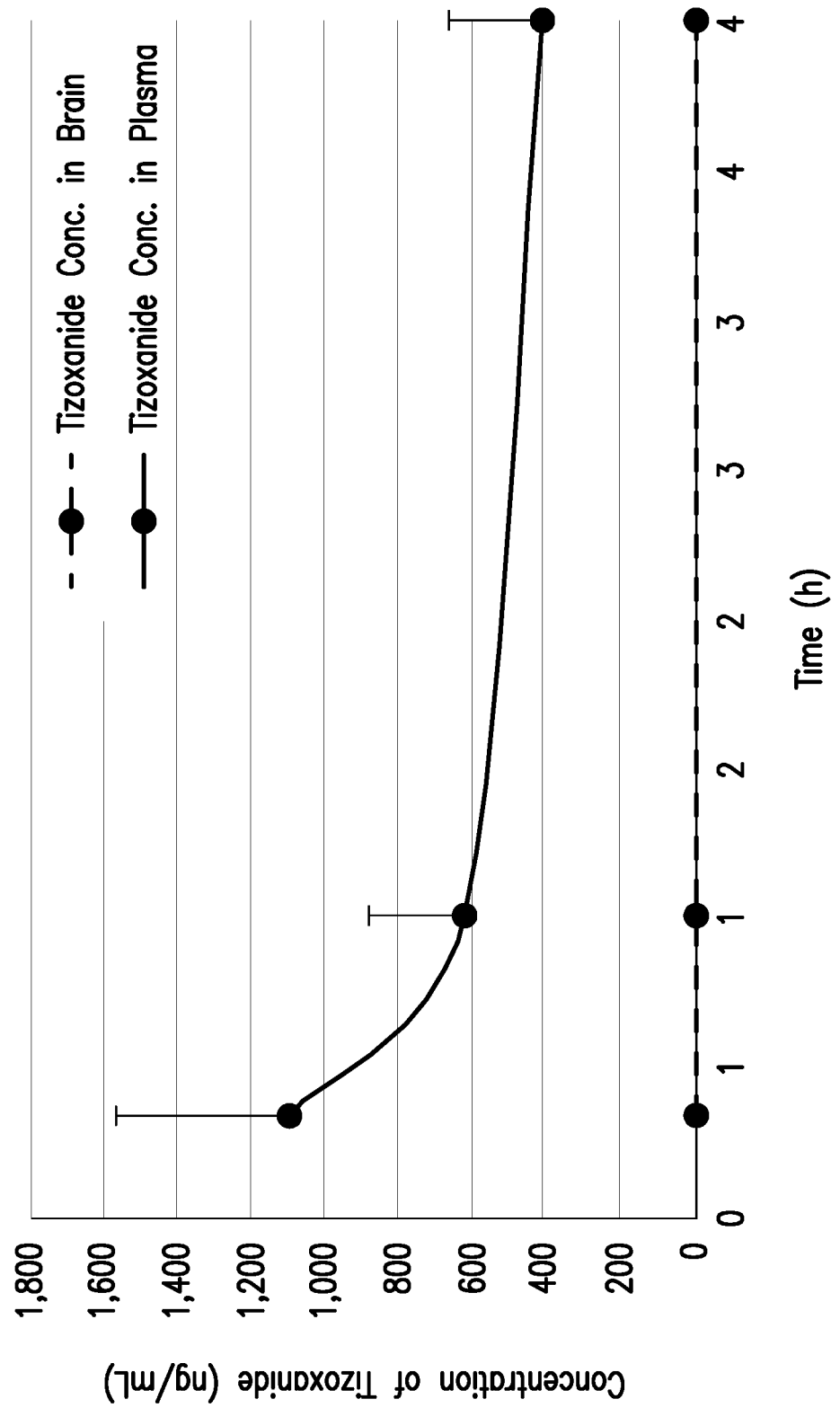
FIG. 4 is a graph reporting exemplary data of concentration of Tizoxanide (TIZ) in plasma and brain tissue of rats after oral administration of Nitazoxanide (NTZ)
Figure 5:
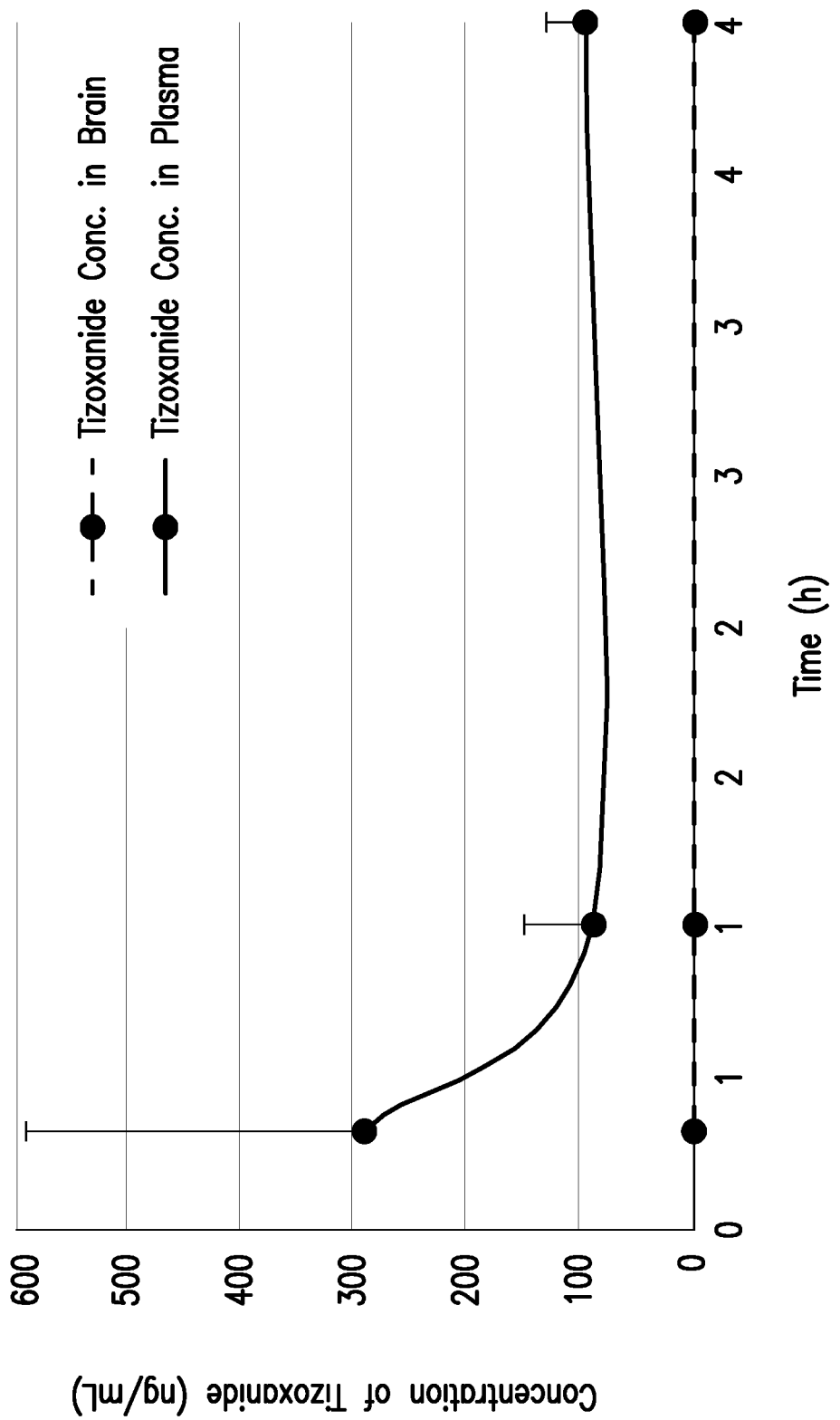
FIG. 5 is a graph reporting exemplary data of concentration of Tizoxanide (TIZ) in plasma and brain tissue of mice after oral administration of Nitazoxanide (NTZ).

An Nitazoxanide (NTZ) pill (Alinia) solution was prepared at a concentration of 14.5 mg/mL (10.0 mg/mL as Nitazoxanide (NTZ) for oral administration (per os, PO), ad libitum, in a mixture of 0.5% methyl cellulose and 99.5% saline. The PO dosing volume was 10 mL/kg. SD rats (n=3 per time point; weighing 0.161 to 0.171 kg) were fasted and oral administration was given using a gavage needle. Blood samples were collected from jugular vein and brain tissues were sampled at 0.33, 1 and 4 hrs after oral administration. Blood samples were centrifuged immediately and a 100 ul aliquot of plasma, and the brain tissues were stored −20° C. until the analysis. The concentration of Nitazoxanide (NTZ) and Tizoxanide (TIZ) in plasma and brain were determined by HPLC/MS/MS analysis. An Agilent 1200 HPLC with Zorbax C18 column and an API4000 tandem quadrupole mass spectrometer were used. The molecular ions of Nitazoxanide (NTZ), Tizoxanide (TIZ) and an internal standard (Chlorzoxazone) were fragmented and detected by monitoring the transitions for each compound. Peak areas were integrated using Analyst software version 1.5.1. (Applied Biosystems). The quantifiable range was from 0.001 to 3 µg/ml for plasma and brain samples. Plasma or brain concentration-time profile for each rat was analyzed (WinNonlin 4.1 program) to obtain pharmacokinetic profile parameters. Brain and plasma concentration-time profiles and pharmacokitentic parameters of Tizoxanide (TIZ) following oral administration of Nitazoxanide (NTZ) pill to rat are shown in FIG. 4. Nitazoxanide (NTZ) could not be quantified in the oral administration. After the oral administration of 145 mg/ml (100 mg/ml as a Nitazoxanide, NTZ), the peak plasma and brain concentration (Cmax) of Tizoxanide (TIZ) in rat was 266.38 and 18.27 ng/ml. reached at 0.39 and 0.55 hrs after administration. Brain/plasma ratio was 0.008, indicating that Tizoxanide (TIZ) unlikely penetrates into the brain (very low positive levels in the brain is considered to be from micro blood vessel included in the brain tissue).

Table 5 reports exemplary results of parameters of pharmacokinetics of Tizoxanide (TIZ) after oral administration of Nitazoxanide (NTZ) pill (Alinia) in rat.

TABLE 5

Exemplary results of parameters of pharmacokinetics of Tizoxanide (TIZ) after oral administration of Nitazoxanide (NTZ) pill (Alinia) in rat.

| Parameters | Plasma | Brain |
|---|---|---|
| $T_{max}$ (h) | 0.55 ± 0.39 | 0.53 ± 0.39 |
| $C_{max}$ (ng/mL) | 1218.00 ± 266.39 | 18.29 ± 10.10 |
| $T_{1/2}$ (h) | *3.86 ± 3.24 | *2.85 ± 2.34 |
| $AUC_{last}$ (ng · h/mL) | 2322.10 ± 603.174 | 17.91 ± 14.59 |
| $AUC_{0-\infty}$ (ng · h/mL) | *5421.14 ± 37.25 | *62.81 ± 36.15 | wherein $C_{max}$ indicates maximum plasma concentration observed, $T_{max}$ indicates time to $C_{max}$, $AUC_{last}$ indicates the Area Under the Curve from zero to the last time point, $AUC_{0-\infty}$ indicates the total area under the plasma concentration time curve from zero to infinity, and $T_{1/2}$ indicates terminal elimination half-life. Values indicated by an asterisk (*) may not be reliable. Brain/Plasma ratio was calculated using the formula: (Brain $AUC_{last}$)/(Plasma $AUC_{last}$).

Example 4. Pharmacokinetics of Tizoxanide (TIZ) after Oral Administration of Nitazoxanide (NTZ) Pill (Alinia) in Mouse Pharmacokinetic studies of Nitazoxanide (NTZ) and Tizoxanide (TIZ) was performed in fasted ICR mice following a protocol similar to that described in Example 3. The results are reported in FIG. 5. After oral administration of 145 mg/mL (100 mg/mL as Nitazoxanide (NTZ pill), the respective peak plasma and brain concentrations ($C_{max}$) of Tizoxanide (TIZ) in mouse were 228.50 and 5.91 ng/ml, which were reached at 0.67 and 1.78 hours after administration, respectively. Brain/plasma ratio was 0.015, indicating that Tizoxanide (TIZ) unlikely penetrates into the brain similar to the finding in rat.

Table 6 reports exemplary results of parameters of pharmacokinetics of Tizoxanide (TIZ) after oral administration of Nitazoxanide (NTZ) pill (Alinia) in mouse.

TABLE 6

Exemplary results of parameters of pharmacokinetics of Tizoxanide (TIZ) after oral administration of Nitazoxanide (NTZ) pill (Alinia) in mouse.

| Parameters | Plasma | Brain |
|---|---|---|
| $T_{max}$ (h) | 0.67 ± 0.39 | 1.55 ± 2.12 |
| $C_{max}$ (ng/mL) | 288.50 ± 227.73 | 5.89 ± 6.21 |
| $T_{1/2}$ (h) | *3.80 ± 1.99 | *1.15 ± 0.49 |
| $AUC_{last}$ (ng · h/mL) | 485.05 ± 162.88 | 7.18 ± 5.62 |
| $AUC_{0-\infty}$ (ng · h/mL) | *1002.85 ± 282.66 | *9.06 ± 9.18 | wherein $C_{max}$ indicates maximum plasma concentration observed, $T_{max}$ indicates time to $C_{max}$, $AUC_{last}$ indicates the Area Under the Curve from zero to the last time point, $AUC_{0-\infty}$ indicates the total area under the plasma concentration time curve from zero to infinity, and $T_{1/2}$ indicates terminal elimination half-life. Values indicated by an asterisk (*) may not be reliable. Brain/Plasma ratio was calculated using the formula: (Brain $AUC_{last}$)/(Plasma $AUC_{last}$).

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

Various publications, patents and patent applications, and protocols are cited herein, the contents of which are hereby incorporated by reference in their entireties.

What is claimed is:

1. A method of treating a cognitive disorder in a subject in need thereof, comprising orally administering to the subject an effective amount of a Nitazoxanide (NTZ) analog having Formula I:

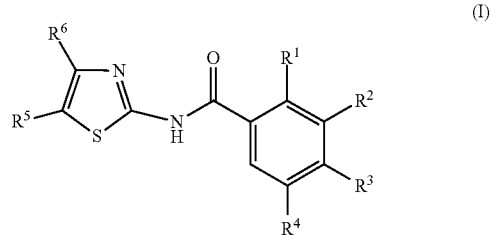

(I)

or a metabolite thereof
wherein:
$R^1$ is selected from the group consisting of H, OH, OC(O)CH$_3$, and OC(O)CH$_2$CH$_3$;
$R^2$, $R^3$, and $R^4$ are independently selected from the group consisting of H, CH$_3$, OH, OCH$_3$, OC(O)CH$_3$, and halogen;
$R^5$ is selected from the group consisting of H, NO$_2$, halogen, optionally substituted alkyl, optionally substituted aryl, optionally substituted amido, optionally substituted sulfonyl, cyano, optionally substituted carboxy, and CF$_3$; and
$R^6$ is selected from the group consisting of H, Ph, and SO$_2$Me;
or a salt, polymorph, solvate, hydrate, N-oxide, or co-crystal thereof,
wherein administering to the subject an effective amount of the Nitazoxanide (NTZ) analog ameliorates a spatial working memory deficit in the subject.

2. The method of claim 1, wherein $R^5$ of the Nitazoxanide (NTZ) analog is selected from the group consisting of H, NO$_2$, iPr, C$_6$H$_4$Cl, NHAc, SO$_2$CH$_3$, CN, CO$_2$CH$_3$, CF$_3$, and Cl.

3. The method of claim 1, wherein the Nitazoxanide (NTZ) analog having Formula I or a metabolite thereof is Nitazoxanide (NTZ).

4. The method of claim 1, wherein the effective amount of Nitazoxanide (NTZ) is 0.1 mg per day to 2000 mg per day.

5. The method of claim 1, wherein the cognitive disorder is Alzheimer's disease, prodromal Alzheimer's disease, dementia, degenerative disorders associated with learning, learning disabilities, memory or cognitive dysfunction, mild cognitive impairment, age-related cognitive decline, cerebral senility, vascular dementia, AIDS-associated dementia, memory impairment associated with depression or anxiety, Down's syndrome, stroke, traumatic brain injury, Huntington's disease, or attention deficit disorder, dementia lacking distinctive histology, progressive supranuclear palsy, corticobasal degeneration, argyrophilic grain disease, multiple system atrophy, amyotrophic lateral sclerosis, ataxia, familial British dementia, thyroid disorders, neurodegeneration with brain iron accumulation type 1, cerebral lipidoses, Tay-Sachs disease, Sandhoff disease, Gaucher disease, Niemann-Pick disease, Krabbe disease, neuronal ceroid lipofuscinoses, cerebrotendinous xanthomatosis, dementia in hepatic and renal failure, dementiabdue to chronic hypovitaminosis, metachromatic leukodystrophy, adrenoleukodystrophy, head trauma, Wernicke-Korsakoff syndrome, cerebral autosomal dominant arteriopathy with subcortical infarcts and leukoencephalopathy, Binswanger disease, cerebral amyloid angiopathy, cognitive dysfunction in multiple sclerosis, or normal pressure hydrocephalus.

6. The method of claim 1, wherein the Nitazoxanide (NTZ) analog having Formula I or a metabolite thereof has negligible bioavailability in brain.

7. The method of claim 1, wherein the Nitazoxanide (NTZ) analog having Formula I or a metabolite thereof has a plasma concentration and a brain concentration, and the ratio between the plasma concentration and the brain concentration is less than 0.02.

8. The method of claim 1, wherein the Nitazoxanide (NTZ) analog having Formula I or a metabolite thereof has a plasma concentration and a brain concentration, and the brain concentration is negligible when the plasma concentration is below about 300 ng/mL.

9. The method of claim 1, wherein the Nitazoxanide (NTZ) analog having Formula I or a metabolite thereof is Tizoxanide (TIZ).

10. A method of improving spatial working memory in a subject in need thereof, comprising administering to the subject an effective amount of a Nitazoxanide (NTZ) analog having Formula I:

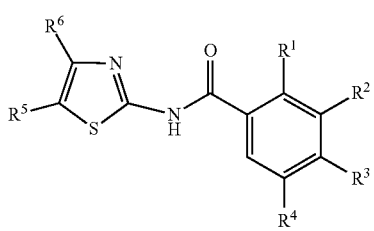

(I)

wherein:
$R^1$ is selected from the group consisting of H, OH, $OC(O)CH_3$, and $OC(O)CH_2CH_3$;
$R^2$, $R^3$, and $R^4$ are independently selected from the group consisting of H, $CH_3$, OH, $OCH_3$, $OC(O)CH_3$, and halogen;
$R^5$ is selected from the group consisting of H, $NO_2$, halogen, optionally substituted alkyl, optionally substituted aryl, optionally substituted amido, optionally substituted sulfonyl, cyano, optionally substituted carboxy, and $CF_3$; and
$R^6$ is selected from the group consisting of H, Ph, and $SO_2Me$;
or a salt, polymorph, solvate, hydrate, N-oxide, or cocrystal thereof.

11. The method of claim 10, wherein $R^5$ of the Nitazoxanide (NTZ) analog is selected from the group consisting of H, $NO_2$, iPr, $C_6H_4Cl$, NHAc, $SO_2CH_3$, CN, $CO_2CH_3$, $CF_3$, and Cl.

12. The method of claim 10, wherein the Nitazoxanide (NTZ) analog having Formula I or a metabolite thereof is Nitazoxanide (NTZ).

13. The method of claim 10, wherein the effective amount of Nitazoxanide (NTZ) is 0.1 mg per day to 2000 mg per day.

14. A method of improving performance in at least one cognitive test by a subject in need thereof, the method comprising administering to the subject an effective amount of a Nitazoxanide (NTZ) analog having Formula I:

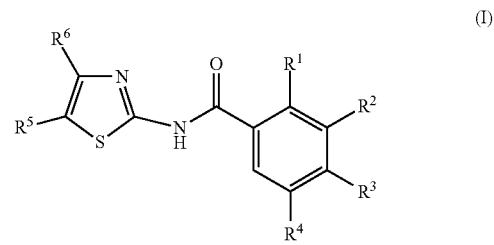

(I)

wherein:
$R^1$ is selected from the group consisting of H, OH, $OC(O)CH_3$, and $OC(O)CH_2CH_3$;
$R^2$, $R^3$, and $R^4$ are independently selected from the group consisting of H, $CH_3$, OH, $OCH_3$, $OC(O)CH_3$, and halogen;
$R^5$ is selected from the group consisting of H, $NO_2$, halogen, optionally substituted alkyl, optionally substituted aryl, optionally substituted amido, optionally substituted sulfonyl, cyano, optionally substituted carboxy, and $CF_3$; and
$R^6$ is selected from the group consisting of H, Ph, and $SO_2Me$;
or a salt, polymorph, solvate, hydrate, N-oxide, or cocrystal thereof,
wherein administering to the subject an effective amount of the Nitazoxanide (NTZ) analog ameliorates a spatial working memory deficit in the subject.

15. The method of claim 14, wherein $R^5$ of the Nitazoxanide (NTZ) analog is selected from the group consisting of H, $NO_2$, iPr, $C_6H_4Cl$, NHAc, $SO_2CH_3$, CN, $CO_2CH_3$, $CF_3$, and Cl.

16. The method of claim 14, wherein the Nitazoxanide (NTZ) analog having Formula I or a metabolite thereof is Nitazoxanide (NTZ).

17. The method of claim 14, wherein the effective amount of Nitazoxanide (NTZ) is 0.1 mg per day to 2000 mg per day.

18. The method of claim 14, wherein the cognitive test is a mini-mental state exam, a mini-cog test, a motor screening task, a paired associates learning test, a spatial working memory test, a reaction time test, a rapid visual information processing test, a delayed matching to sample test, a pattern recognition memory test, or an Automated Neuropsychological Test Battery (CANTAB).

* * * * *